United States Patent
Adachi et al.

(10) Patent No.: US 9,712,931 B2
(45) Date of Patent: *Jul. 18, 2017

(54) HEARING AID GAIN DETERMINATION SYSTEM, HEARING AID GAIN DETERMINATION METHOD, AND COMPUTER PROGRAM

(71) Applicant: Panasonic Corporation, Osaka (JP)

(72) Inventors: Shinobu Adachi, Nara (JP); Koji Morikawa, Kyoto (JP); Jun Ozawa, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 104 days.

This patent is subject to a terminal disclaimer.

(21) Appl. No.: 14/137,802

(22) Filed: Dec. 20, 2013

(65) Prior Publication Data

US 2014/0105436 A1 Apr. 17, 2014

Related U.S. Application Data

(63) Continuation of application No. PCT/JP2013/002287, filed on Apr. 2, 2013.

(30) Foreign Application Priority Data

Apr. 24, 2012 (JP) .................................. 2012-098430

(51) Int. Cl.
*A61B 5/048* (2006.01)
*H04R 25/00* (2006.01)
(Continued)

(52) U.S. Cl.
CPC ......... *H04R 25/70* (2013.01); *A61B 5/04845* (2013.01); *A61B 5/121* (2013.01);
(Continued)

(58) Field of Classification Search
CPC ........... A61B 5/12; A61B 5/048; A61B 5/486; A61B 5/0476; A61B 5/0478;
(Continued)

(56) References Cited

U.S. PATENT DOCUMENTS

| 2,511,482 | A | * | 6/1950 | Shaper | ..................... A61B 5/12 369/174 |
| 4,275,744 | A | * | 6/1981 | Thornton | ........... A61B 5/04845 600/544 |

(Continued)

FOREIGN PATENT DOCUMENTS

| JP | 2010-504139 T | 2/2010 |
| WO | WO 2001/087147 A2 | 11/2001 |

(Continued)

OTHER PUBLICATIONS

Woods et al, The Habituation of Evenet related Potentials to Speech Sounds and Tone; The Electroencephalography and clinical Neurophysiology, Elsevier Scientific Publishers; 1986, 65; p. 447-459.*

(Continued)

*Primary Examiner* — Davetta W Goins
*Assistant Examiner* — Oyesola C Ojo
(74) *Attorney, Agent, or Firm* — Renner, Otto, Boisselle & Sklar, LLP

(57) ABSTRACT

A hearing aid gain determination system includes: a biological signal measurement section for measuring an electroencephalogram signal; a sound group determination section for determining a frequency of a sound group including first, second and third sounds; a sound pressure determination section for determining sound pressures of the first to third sounds so that the respective sound pressures are less than a threshold and that the first to third sounds consecutively decrease; an output section for presenting the first to (Continued)

RIGHT EAR

LEFT EAR third sounds at the determined frequency and sound pressures; a characteristic amount extraction section for extracting a characteristic amount concerning time-frequency information of an event-related potential in a time range after presenting the first to third sounds; a gain determination section for determining a hearing aid gain for the frequency of the sound stimulation group against a predetermined criterion based on the characteristic amounts.

20 Claims, 14 Drawing Sheets

(51) Int. Cl.
    *A61B 5/00*         (2006.01)
    *A61B 5/0484*     (2006.01)
    *A61B 5/12*         (2006.01)

(52) U.S. Cl.
    CPC .............. *A61B 5/72* (2013.01); *A61B 5/7282* (2013.01); *A61B 5/125* (2013.01); *A61B 5/7257* (2013.01)

(58) Field of Classification Search
    CPC ..... A61B 5/0482; A61B 5/04845; A61B 5/72; A61B 5/7282; H04R 25/70
    USPC .................................. 381/104, 321; 600/559
    See application file for complete search history.

(56) References Cited

U.S. PATENT DOCUMENTS

| | | | | |
|---|---|---|---|---|
| 5,230,344 | A * | 7/1993 | Ozdamar | A61B 5/0478 600/544 |
| 5,954,667 | A * | 9/1999 | Finkenzeller | A61B 5/04845 600/544 |
| 5,999,856 | A * | 12/1999 | Kennedy | A61N 1/36032 381/60 |
| 8,177,727 | B2 * | 5/2012 | Kwak | A61B 5/04845 600/544 |
| 2001/0049480 | A1 * | 12/2001 | John | A61B 5/04845 600/559 |
| 2004/0064066 | A1 | 4/2004 | John et al. | |
| 2004/0204659 | A1 | 10/2004 | John et al. | |
| 2005/0043646 | A1 * | 2/2005 | Viirre | A61B 5/0482 600/545 |
| 2007/0191727 | A1 * | 8/2007 | Fadem | A61B 5/0002 600/544 |
| 2008/0037797 | A1 * | 2/2008 | Goldstein | A61B 5/121 381/56 |
| 2009/0163828 | A1 * | 6/2009 | Turner | A61B 5/04845 600/559 |
| 2009/0247895 | A1 * | 10/2009 | Morikawa | A61B 5/04842 600/544 |
| 2009/0292221 | A1 * | 11/2009 | Viirre | A61B 5/0482 600/544 |
| 2010/0076338 | A1 | 3/2010 | Kwak | |
| 2010/0076339 | A1 * | 3/2010 | Marcoux | A61B 5/04845 600/559 |
| 2011/0188664 | A1 * | 8/2011 | Morikawa | A61B 5/04845 381/60 |
| 2011/0299709 | A1 * | 12/2011 | Anderson | A61B 5/121 381/315 |

FOREIGN PATENT DOCUMENTS

| | | |
|---|---|---|
| WO | WO 2008/038650 A1 | 4/2008 |
| WO | WO 2011/001694 A1 | 1/2011 |

OTHER PUBLICATIONS

International Search Report for corresponding International Application No. PCT/JP2013/002287 mailed Jun. 18, 2013.

Nobuo Adachi et al., "Jun'on Pair Shigeki ni Taisuru Yuhatsu Den'i ni Motozuku Fukai On'atsu Level Suitei", Japanese Journal of Clinical Neurophysiology, Oct. 1, 2011 (Oct. 1, 2011), vol. 39, No. 5, p. 447.

Thornton, A.R. et al., "The objective estimation of loudness discomfort level using auditory brainstem evoked responses", MRC Institute of Hearing Research, 1987; 16(4):219-25.

Jishoukanrendeni (ERP) Manyuaru—P300 Wo Chushinni—(or "Event-Related Potential (ERP) Manual—mainly concerning P300-"), edited by Kimitaka Kaga et al., Shinohara Shuppan Shinsha, 1995), p. 30 and concise explanation.

D.P. Pascoe, "Clinical measurements of the auditory dynamic range and their relation to formulas for hearing aid gain", In lensen. H. I. (Ed.) Hearing Aid Fitting: Theoretical and Practical Views 13th Danavox Symposium. Copenhagen: Stougaard, 1988.

Kazuoki Kodera, Hochoki Fittingu No Kangaekata (or "Concept of Hearing Aid Fitting"), 3rd edit., Nov. 11, 2010, p. 81 and concise explanation.

* cited by examiner

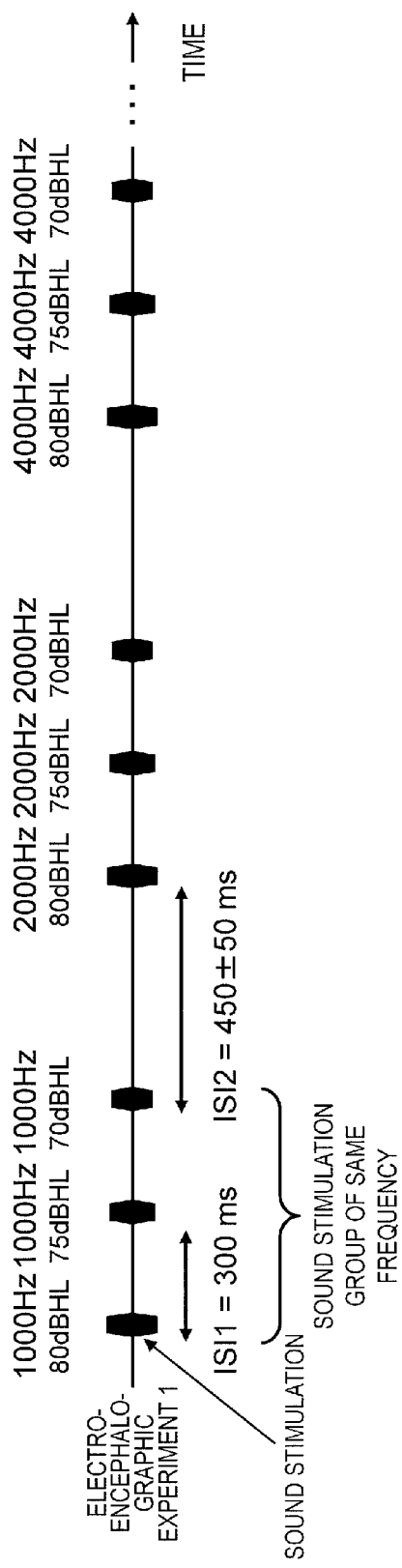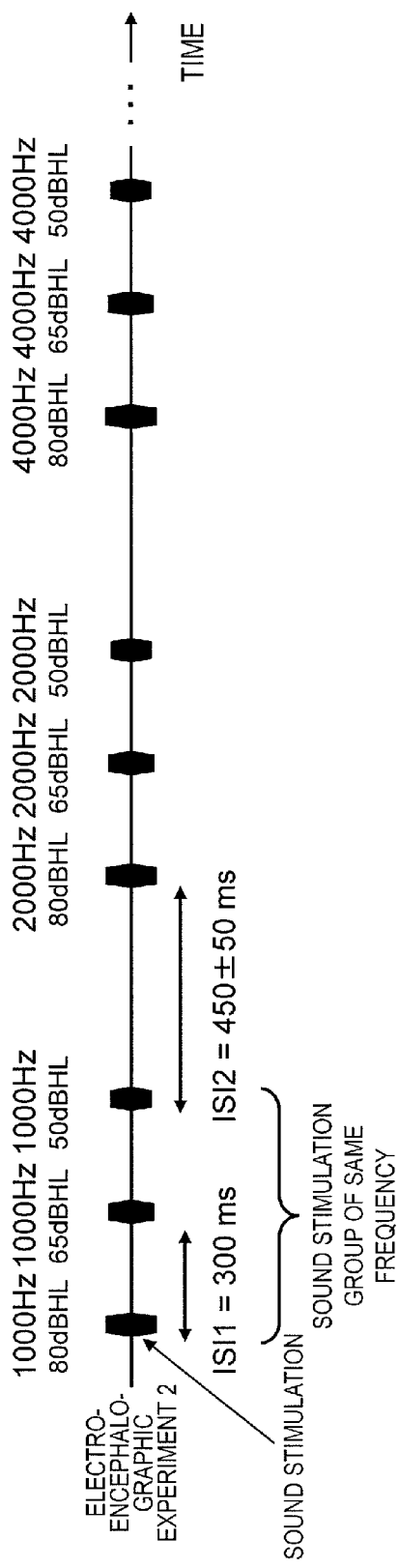

UPPER VIEW     FRONTAL VIEW

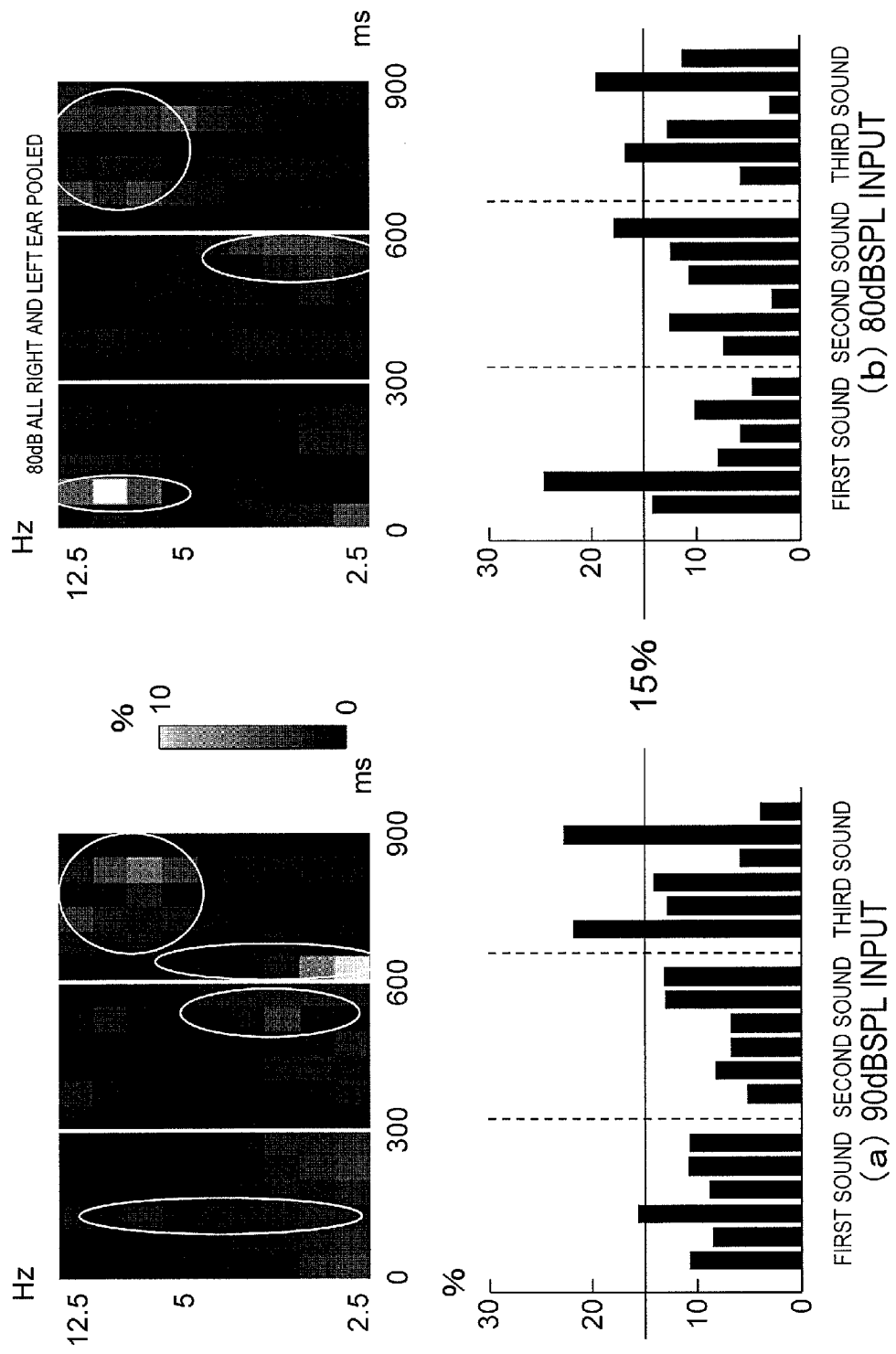

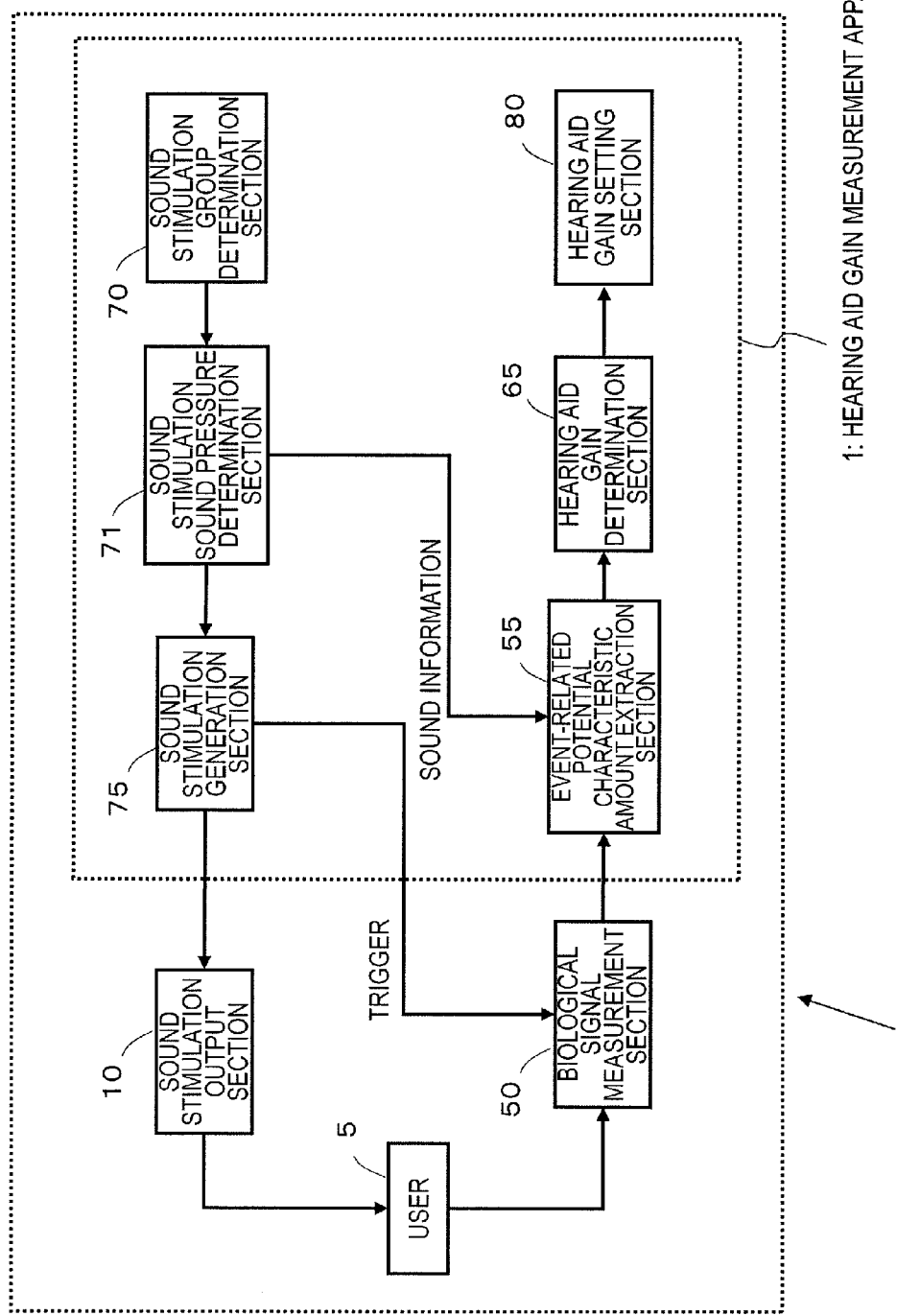

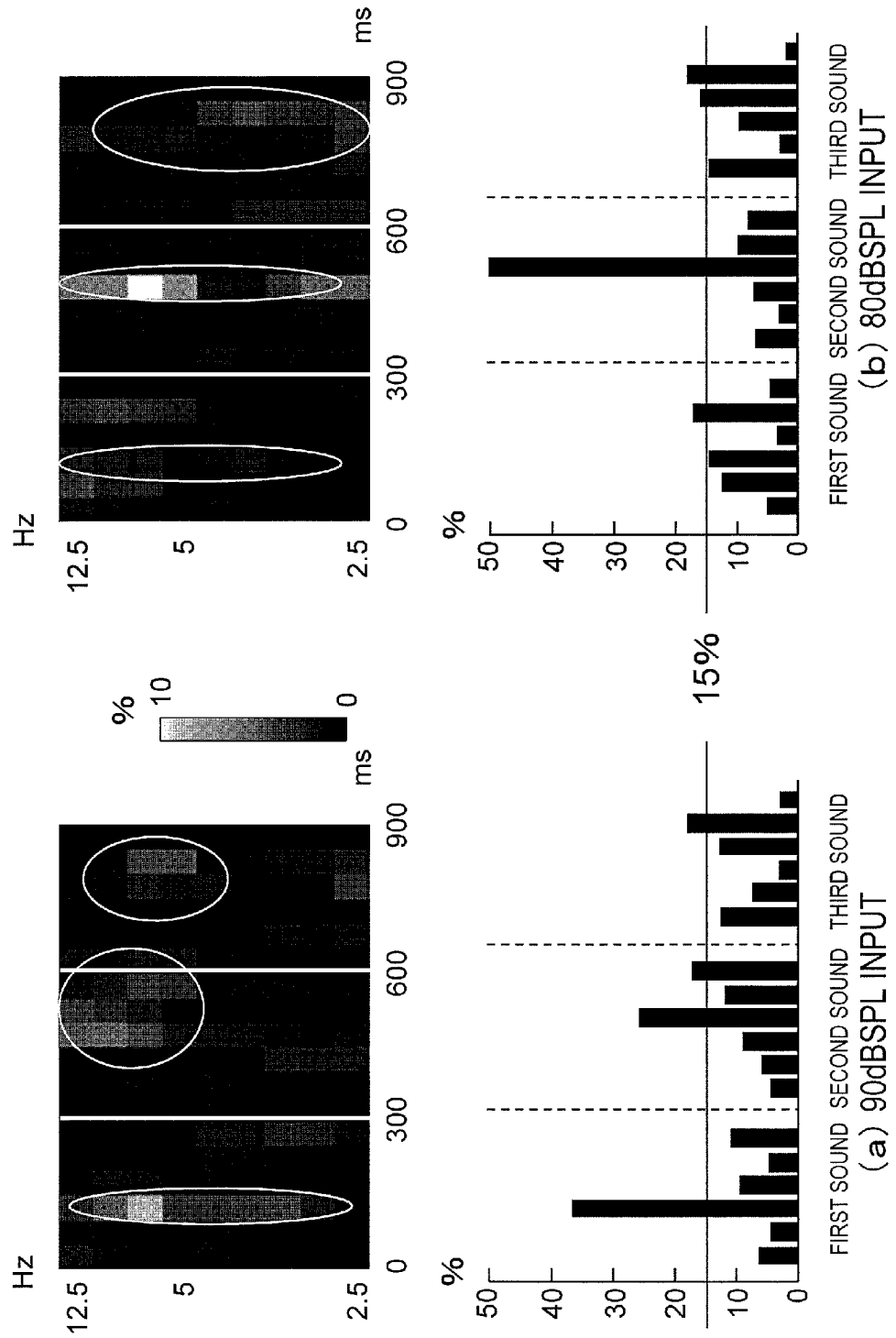

HEARING AID GAIN DETERMINATION SYSTEM, HEARING AID GAIN DETERMINATION METHOD, AND COMPUTER PROGRAM

This is a continuation of International Application No. PCT/JP2013/002287, with an international filing date of Apr. 2, 2013, which claims priority of Japanese Patent Application No. 2012-098430, filed on Apr. 24, 2012, the contents of which are hereby incorporated by reference.

BACKGROUND

1. Technical Field

The present application relates to a hearing aid fitting technique. More specifically, it relates to a system, method, and program for determining the sound gain of a hearing aid, during hearing aid fitting.

2. Description of the Related Art

Hypacusia means difficulty in hearing sounds of a specific frequency or a frequency band, for example. The frequency or frequency band which presents hearing difficulty differs from user to user.

A hearing aid amplifies sounds so that the user can hear the sounds. The necessary amount of amplification differs for each user because auditory characteristics are different from user to user. In the present specification, "gain" means an amount by which a sound is to amplified (amount of gain).

Prior to beginning use of a hearing aid, fitting is conducted to determine a gain for each sound frequency. In order to perform appropriate fitting, it is necessary to accurately measure the auditory characteristics of a user.

In an auditory characteristics test, a hearing threshold level (HTL) is determined first. Next, an uncomfortable level (UCL) is determined. The HTL and the UCL are used for determining a dynamic range of sound pressure for sounds to be output from a hearing aid.

It is also possible to measure UCL by using electroencephalogram. For example, Thornton, A. R. et al, "The objective estimation of loudness discomfort level using auditory brainstem evoked responses", Scandinavian Audiology, Vol. 16, No. 4, P. 219-225, 1987 (refereed to as Non-Patent Document 1 hereinafter), discloses that there is correlation between a V wave latency of an auditory brainstem response (ABR) to a click sound and the UCL.

Currently, several fitting theories are proposed in order to derive a gain for each frequency of a hearing aid or for each sound pressure of an input sound. For example, in the half-gain method, the gain of each frequency is made half of the HTL for that frequency. Berger's method slightly augments the amplification from 1000 Hz to 4000 Hz by taking into consideration the frequency band of the conversational voice. The POGO method reduces the gains at 250 Hz and 500 Hz by 10 dB and 5 dB, respectively. The NAL-R method performs amplification so that a frequency of long-term sound analysis of words will fall around a comfortable level.

SUMMARY

Although the construction disclosed in Non-Patent Document 1 enables UCL estimation, it cannot directly estimate a gain of a hearing aid for each frequency. Under the aforementioned various fitting theories, while it is possible to determine the gain of a hearing aid that is universally calculated from auditory characteristics, it is impossible to set a gain that is suitable for each user.

One non-limiting, and exemplary embodiment of the present application provides a system, method, and computer program which estimates the auditory characteristics of a user from a measured electroencephalogram, and based on the estimated auditory characteristics, determines a hearing aid gain for each frequency band such that the gain is suitable for that user.

In one general aspect, a hearing aid gain determination system disclosed herein comprises: a biological signal measurement section for measuring an electroencephalogram signal of a user; a sound stimulation group determination section for determining a frequency of a sound stimulation group including a first sound, a second sound, and a third sound, the first to third sounds being pure tones; a sound pressure determination section for determining sound pressures of the first sound, the second sound, and the third sound so that the respective sound pressures are equal to or less than a predetermined threshold value and that the first sound, the second sound, and the third sound consecutively decrease in sound pressure in this order; an output section for presenting the first sound, the second sound, and the third sound to the user at the frequency and sound pressures determined by the sound stimulation group determination section and the sound pressure determination section; a characteristic amount extraction section for extracting a characteristic amount concerning time-frequency information of an event-related potential in the electroencephalogram signal in a predetermined time range beginning after a point of presenting each of the first sound, the second sound, and the third sound; and a gain determination section for, based on the characteristic amounts extracted by the characteristic amount extraction section, determining a hearing aid gain for the frequency of the sound stimulation group against a predetermined criterion.

According to the above aspect, it is possible to estimate a hearing aid output for each frequency, given a frequency.

This general and particular aspect can be implemented as a system, a method, a computer program or a combination thereof.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIGS. 2A and 2B are diagrams showing exemplary sound stimulations used in an electroencephalographic experiment conducted by the inventors.

FIG. 7 shows graphs showing exemplary occurrence frequencies of wavelet coefficients used in the upper 1% exhibiting least average errors, in the hearing aid output estimation of Electroencephalogram measurement experiment 1.

FIG. 8 is a diagram showing the construction of an implementation of a hearing aid gain determination system according to Embodiment 1.

FIG. 15 shows graphs showing exemplary occurrence frequencies of wavelet coefficients used in the upper 1% exhibiting least average errors, in the hearing aid output estimation of Electroencephalogram measurement experiment 2.

DETAILED DESCRIPTION

Figure 1A:
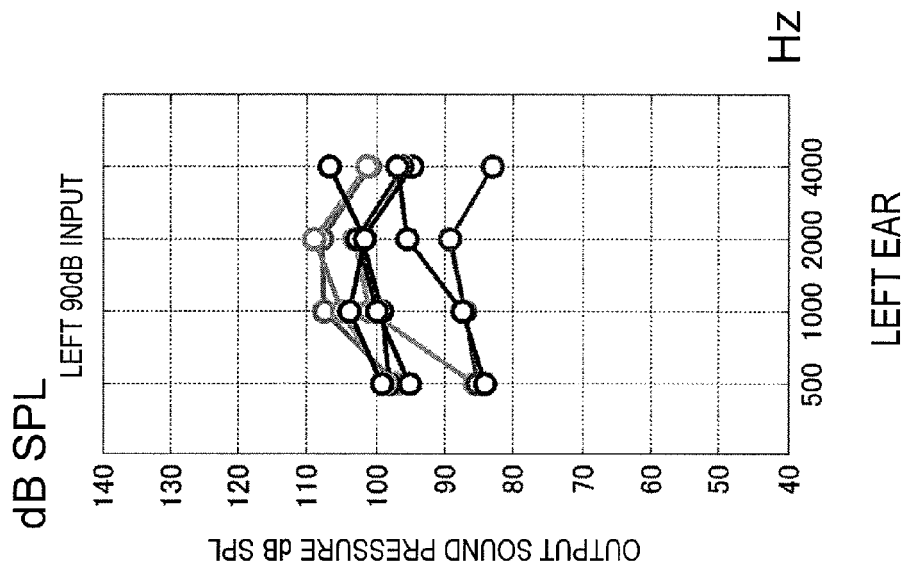
FIGS. 1A and 1B are diagrams showing exemplary hearing aid outputs under a 90 dBSPL input, as exemplary results of a hearing aid characteristics measuring experiment conducted by the inventors.

A first embodiment according to the present disclosure is a hearing aid gain determination system comprising: a biological signal measurement section configured to measure an electroencephalogram signal of a user; a sound stimulation group determination section configured to determine a frequency of a sound stimulation group including a first sound, a second sound, and a third sound, the first to third sounds being pure tones; a sound pressure determination section configured to determine sound pressures of the first sound, the second sound, and the third sound so that the respective sound pressures are equal to or less than a predetermined threshold value and that the first sound, the second sound, and the third sound consecutively decrease in sound pressure in this order; an output section configured to present the first sound, the second sound, and the third sound to the user at the frequency and sound pressures determined by the sound stimulation group determination section and the sound pressure determination section; a characteristic amount extraction section configured to extract a characteristic amount concerning time-frequency information of an event-related potential in the electroencephalogram signal in a predetermined time range beginning after a point of presenting each of the first sound, the second sound, and the third sound; and a gain determination section configured to determine a hearing aid gain for the frequency of the sound stimulation group against a predetermined criterion based on the characteristic amounts extracted by the characteristic amount extraction section.

In a second embodiment according to the present disclosure, the gain determination section determines a hearing aid output under an input sound pressure of 80 dBSPL or more against a predetermined criterion which previously defines associations between the characteristic amounts and hearing aid output values which are set under an input sound pressure of 80 dBSPL or more.

In a third embodiment according to the present disclosure, the gain determination section determines a hearing aid output under an input sound pressure having a 90 dBSPL or 80 dBSPL against a predetermined criterion which previously defines associations between the characteristic amounts and hearing aid output values under a 90 dBSPL input or a 80 dBSPL input.

In a fourth embodiment according to the present disclosure, the predetermined threshold value is a sound pressure lower than a generic UCL value.

In a fifth embodiment according to the present disclosure, the sound pressure determination section determines the sound pressures of the first sound, the second sound, and the third sound so that the first sound, the second sound, and the third sound consecutively decrease in sound pressure in this order by every 5 dB.

In a sixth embodiment according to the present disclosure, the sound pressure determination section determines the sound pressures of the first sound, the second sound, and the third sound so that the first sound, the second sound, and the third sound consecutively decrease in sound pressure in this order by every 15 dB.

A seventh embodiment according to the present disclosure further comprises a gain setting section configured to, based on a result of determination by the gain determination section, setting a hearing aid gain for each frequency under: a 90 dBSPL input or a 80 dBSPL input; or a 90 dBSPL input and a 80 dBSPL input.

In an eighth embodiment according to the present disclosure, the gain determination section retains, as the predetermined criterion, data which defines associations between time-frequency related characteristic amounts measured of a plurality of users and hearing aid gains under a 90 dBSPL input or a 80 dBSPL input, and determines a hearing aid gain against the predetermined criterion.

In a ninth embodiment according to the present disclosure, the gain determination section retains said predetermined criterions respectively for different frequencies of the sound stimulation group, and uses a selected one of the predetermined criterions in accordance with the frequency of the sound stimulation group.

In a tenth embodiment according to the present disclosure, the characteristic amount extraction section calculates time-frequency information of the electroencephalogram signal in a zone until the lapse of 300 ms since the point of presenting each of the first sound, the second sound, and the third sound, and adopts as a characteristic amount an averaged value over a predetermined frequency range and a predetermined time range.

In an eleventh embodiment according to the present disclosure, the predetermined frequency range is a frequency range defined by dividing a frequency range from 2.5 Hz to 12.5 Hz into nine.

In a twelfth embodiment according to the present disclosure, the predetermined time range is 50 ms.

A thirteenth embodiment according to the present disclosure is a hearing aid gain determination apparatus comprising: a characteristic amount extraction section for, from an electroencephalogram signal of a user measured by a biological signal measurement section, extracting a time-frequency related characteristic amount of an event-related potential in the electroencephalogram signal after a point of presenting each of a first sound, a second sound, and a third sound from an output section, the first sound, the second sound, and the third sound consecutively decreasing in sound pressure in this order such that the respective sound pressures are equal to or less than a predetermined threshold value; and a gain determination section for, based on the characteristic amounts extracted by the characteristic amount extraction section, determining a hearing aid gain against a predetermined criterion.

A fourteenth embodiment according to the present disclosure is a hearing aid gain determination method comprising the steps of: measuring an electroencephalogram signal of a user; determining a frequency of a sound stimulation group including a first sound, a second sound, and a third sound, the first to third sounds being pure tones; determining sound pressures of the first sound, the second sound, and the third sound so that the respective sound pressures are equal to or less than a predetermined threshold value and that the first sound, the second sound, and the third sound consecutively decrease in sound pressure in this order; presenting the first sound, the second sound, and the third sound to the user at the determined frequency and sound pressures; extracting a characteristic amount concerning time-frequency information of an event-related potential in the electroencephalogram signal in a predetermined time range beginning after a point of presenting each of the first sound, the second sound, and the third sound; and based on the extracted characteristic amounts, determining a hearing aid gain against a predetermined criterion.

A fifteenth embodiment according to the present disclosure is a computer program stored on a non-transitory computer-readable medium, and to be executed by a computer mounted in a hearing aid gain determination apparatus of a hearing aid gain determination system, wherein the computer program causes the computer to execute the steps of: determining a frequency of a sound stimulation group including a first sound, a second sound, and a third sound, the first to third sounds being pure tones; determining sound pressures of the first sound, the second sound, and the third sound so that the respective sound pressures are equal to or less than a predetermined threshold value and that the first sound, the second sound, and the third sound consecutively decrease in sound pressure in this order; presenting the first sound, the second sound, and the third sound to a user at the determined frequency and sound pressures; from an electroencephalogram signal of the user when the first sound, the second sound, and the third sound are presented thereto, extracting a characteristic amount concerning time-frequency information of an event-related potential in a predetermined time range beginning after a point of presenting each of the first sound, the second sound, and the third sound; and based on the extracted characteristic amounts, determining a hearing aid gain against a predetermined criterion.

The general and specific embodiment above can be implemented by using a system, an apparatus, a method, or a computer program, or implemented by using a combination of a system, an apparatus, a method, and/or a computer program.

First, the definitions of the terms used in the present specification will be described.

An "event-related potential (ERP)" is a fluctuation in the potential of an electroencephalogram (EEG) that occurs in response to a stimulation, and refers to a transient potential fluctuation in the brain which occurs in temporal relationship with an external stimulation or an internal event.

A "sound stimulation", also referred to as an auditory stimulation, is a sound which is presented to a user.

An "N1 component" is a negative component of event-related potential which appears at about 100 ms since the point of presenting a sound stimulation as a starting point.

A "P2 component" is a positive component of event-related potential which appears at about 200 ms since the point of presenting a sound stimulation as a starting point.

"Latency" is the time, based on the point of presenting an audio stimulation as a starting point, until a peak potential of a positive component or a negative component appears.

A "negative component" generally refers to a potential which is smaller than 0 μV. In a comparison between two potentials, the potential having the greater negative value may be referred to as a negative component between the two.

A "positive component" generally refers to a potential which is greater than 0 μV. In a comparison between two potentials, the potential having the greater value may be referred to as a positive component between the two.

An "input sound pressure" refers to the sound pressure (sound pressure level) of a sound which is input to a hearing aid.

A "hearing aid gain" is an amount by which a hearing aid amplifies a sound, for each sound pressure or each frequency of sounds that may be input to the hearing aid. For example, it corresponds to the difference between the sound pressure (sound pressure level) of a sound which is input to the hearing aid and the sound pressure (sound pressure level) of a sound which is output from the hearing aid.

A "hearing threshold level (HTL)" is the sound pressure of a softest sound that is audible to a user.

A "pure tone" is a tone which repetitively undergoes periodic oscillation, such that it is expressed as a sine wave having only one frequency component.

Generally speaking, there are 30 to 50 ms differences (shifts) in event-related potential waveform between individuals, according to table 1 on p. 30 of "JISHOUKAN-RENDENI (ERP) MANYUARU—P300 WO CHUSH-INNI—(or "Event-Related Potential (ERP) Manual— mainly concerning P300—"), edited by Kimitaka KAGA et al., Shinohara Shuppan Shinsha, 1995)". Therefore, in the present specification, the expression "about X ms" or "near X ms" may be interpreted as encompassing a breadth of 30 to 50 ms before or after X ms (e.g., 100 ms±30 ms for an N1 component and 200 ms±50 ms for a P2 component).

Hereinafter, each embodiment will be described with reference to the drawings.

A hearing aid gain determination system according to the present embodiment presents a sound, and by using an event-related potential of a user in response to the presented sound, estimates an amount by which sound is to be amplified by a hearing aid. Specifically, the hearing aid gain determination system, estimates the sound pressure of a sound which is to be output after adjustment by a hearing aid, for each sound frequency or each sound pressure.

Prior to describing the estimation technique, experiments which have been conducted by the inventors and the experimental results thereof will be described. More specifically, the characteristics of event-related potential that enable hearing aid gain determination, which the inventors have found from the experimental data, will be described.

(Description of Experimental Outline)

1. Experimental Outline

The inventors have conducted the following two experiments for hearing aid users, in order to estimate an appropriate hearing aid gain for each frequency, given a predetermined input sound pressure.

One is a hearing aid characteristics measuring experiment of measuring characteristics of a hearing aid which is daily used by a hearing aid user. The hearing aid characteristics measuring experiment was conducted by using a special apparatus for hearing aid characteristics measurement (FO-NIX FP35).

Another is an electroencephalogram measurement experiment of measuring responses to sound stimulations. The electroencephalogram measurement experiment was conducted under two kinds of sound stimulation settings.

In each of Electroencephalogram measurement experiment 1 and Electroencephalogram measurement experiment 2, a first sound, a second sound, and a third sound were presented to each experimental participant as one set, with a predetermined time interval between them. The first sound, the second sound, and the third sound were pure tones of the same frequency. In the present specification, one set of sound stimulations (first sound, second sound, and third sound) having the same frequency may be referred to as a "sound stimulation group".

In Electroencephalogram measurement experiment 1, the first sound was 80 dBHL, the second sound was 75 dBHL, and the third sound was 70 dBHL. In other words, the first to third sounds consecutively decreased in sound pressure by every 5 dB.

In Electroencephalogram measurement experiment 2, the first sound was 80 dBHL, the second sound was 65 dBHL, and the third sound was 50 dBHL. In other words, the first to third sounds consecutively decreased in sound pressure by every 15 dB.

In both of Electroencephalogram measurement experiment 1 and Electroencephalogram measurement experiment 2, an event-related potential in response to each of the first to third sounds was measured.

A "pure tone" is a sound which repetitively undergoes periodic oscillation at a single frequency and is expressed as a sine wave. Herein, any sound whose frequency is undergoing changes that are not aurally distinguishable to the human may also be regarded as a sound of a single frequency.

Through Electroencephalogram measurement experiments 1 and 2 above, it was examined whether it would be possible to estimate, from a measured electroencephalogram (event-related potential), a result of hearing aid characteristics measurement when a sound having a sound pressure of 80 dBSPL or more was input (more specifically, under a 90 dBSPL input and under a 80 dBSPL input).

As a result, the inventors have found that, from the electroencephalogram in response to sound stimulations of sound pressures that are lower than a sound pressure which is generally evaluated to be the UCL, a hearing aid gain when 80 dBSPL or more is input (under a 90 dBSPL input and under a 80 dBSPL input) is estimatable with an average error of about 5 dB.

Now will be described a "sound pressure lower" than a sound pressure which is generally evaluated to be the UCL. Generally speaking, a sound pressure lower than a sound pressure which is generally evaluated to be the UCL would fluctuate depending on the HTL value.

UCL sound pressures which are estimated for different HTL values are described in, for example, Pascoe, D. P. (1988). (Clinical measurements of the auditory dynamic range and their relation to formulas for hearing aid gain. In J. H. Jensen. (Ed.) Hearing Aid Fitting: Theoretical and Practical Views 13th Danavox Symposium. Copenhagen: Stougaard.) Based on a UCL which is thus determined from the HTL, any sound pressure which is lower than this UCL by e.g. 5 dB or more may be regarded as the "sound pressure lower than a sound pressure which is generally evaluated to be the UCL".

In order to measure the level of hypacusia of each experimental participant, his or her HTLs at 250 Hz, 500 Hz, 1000 Hz, 2000 Hz, and 4000 Hz were measured in advance.

Hereinafter, particulars of the experiments by the inventors, experimental results, and characteristic features of electroencephalogram that became clear through analysis of the experimental results will be described.

(Description of Experimental Conditions)

2-1. Hearing Aid Characteristics Measuring Experiment And Electroencephalogram Measurement Experiment The experimental participants were 22 people with hypacusia (between 61 and 80; average 73.0) who were wearing a hearing aid(s) on a daily basis. The people with hypacusia consisted of 15 males and 7 females. Among all participants, hearing aids were worn on 18 right ears and 8 left ears (totaling 26 ears). Four people had hearing aids worn on both ears.

By using a method of quartering, an average hearing level of participants was measured. The measurements showed the following hypacusia levels among the 26 ears: 20 ears had medium levels of hypacusia (40 to 69 dBHL); 3 ears had low levels of hypacusia (26 to 39 dBHL); and 3 ears had high levels of hypacusia (70 dBHL or higher).

In a method of quartering, a value which is calculated as $(a+2b+c)/4$ is regarded as an average hearing level. Herein, a is an HTL at 500 Hz; b is an HTL at 1000 Hz; and c is an HTL at 2000 Hz.

2-2. Hearing Aid Characteristics Measuring Experiment

In order to measure the gain of a hearing aid as daily used by each user, the volume was set at the position of daily use.

By using a hearing aid characteristics measurement apparatus, the sound pressure of an output sound from a hearing aid for each of input sounds of 50, 60, 70, 80, and 90 dBSPL was measured. The frequency was measured for input sounds of 200 Hz to 8000 Hz. The sound pressure of the output sound was measured by using a 2 cc coupler.

In order to reduce measurement errors, four measurements were taken for each hearing aid, and an average of output sounds of 500 Hz, 1000 Hz, 2000 Hz, and 4000 Hz was determined.

Figure 1B:
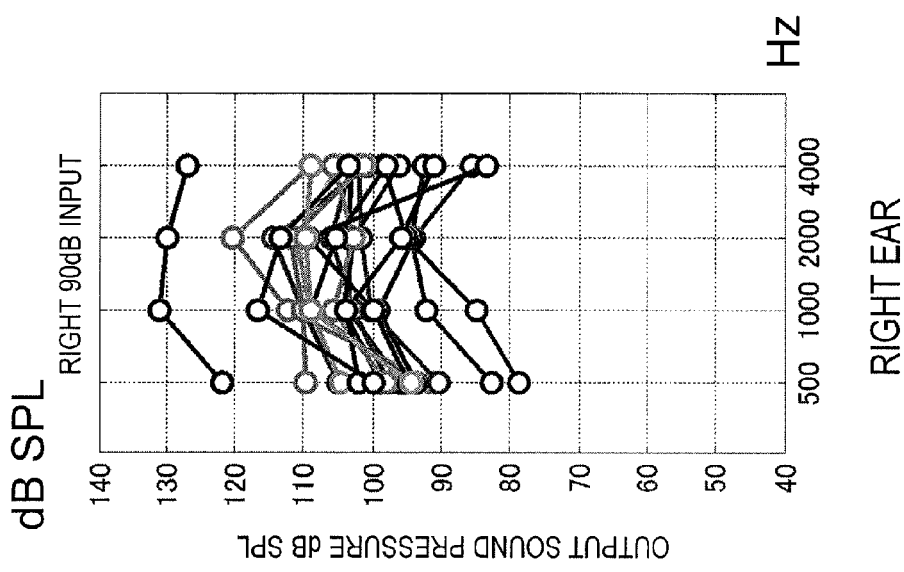

FIGS. 1A and 1B show measurement results of hearing aid output for each participant when a sound of 90 dBSPL is input. In FIGS. 1A and 1B, the horizontal axis represents frequency, and the vertical axis represents sound pressure (dBSPL).

FIG. 1A shows measurement results for the 18 right ears wearing a hearing aid, and FIG. 1B shows measurement results for the 8 left ears wearing a hearing aid. It is clear from FIGS. 1A and 1B that the hearing aid output under a 90 dBSPL input differs from user to user. For example, the results shown in FIG. 1A indicate 40 dB differences of output sound pressure among users for a sound of 500 Hz.

These results indicate that, given the same input sound pressure, the appropriate gain would differ for each user. Similar fluctuations were also observed for the hearing aid output under a 80 dBSPL input. The average and standard deviation of hearing aid outputs at 500, 1000, 2000, and 4000 Hz were, respectively, 96.1±8.8, 103.7±9.4, 105.1±8.7, and 99.6±8.8 dBSPL.

Note that a hearing aid gain can be determined by subtracting the sound pressure of an input sound to a hearing aid from the sound pressure of an output sound from the hearing aid.

2-3. Electroencephalogram Measurement Experiment

In Electroencephalogram measurement experiment 1, three sound stimulations which monotonously decreased in sound pressure in the order of 80 dBHL, 75 dBHL, and 70 dBHL were presented as a sound stimulation group, and characteristic changes in event-related potential from sound stimulation to sound stimulation were examined. The sound stimulation group had one of four frequencies (500, 1000, 2000, 4000 Hz). Sound stimulation groups of different frequencies were successively presented at a predetermined time interval.

Electroencephalogram measurement experiment 2 was conducted under the same conditions as in Electroencephalogram measurement experiment 1, except for the sound pressures of the presented sound stimulations. In Electroencephalogram measurement experiment 2, the sound stimulations were consecutively presented with monotonously decreasing sound pressures at 80 dBHL, 65 dBHL, and 50 dBHL.

Note that the sound pressures of the sounds presented in Experiment 1 and Experiment 2 (80 dBHL, 75 dBHL, 70 dBHL, 65 dBHL, 50 dBHL) were lower than a sound pressure which is generally evaluated to be the UCL.

Hereinafter, with reference to FIGS. 2A and 2B, FIG. 5, and FIG. 13, detailed experimental settings and experimental results of Electroencephalogram measurement experiments 1 and 2 will be described.

Each sound stimulation is a tone burst sound having a rise of 3 ms, a duration 44 ms, and a fall of 3 ms.

The sound stimulations included in the sound stimulation group were presented to the same ear at a predetermined interval. The sound stimulations were output to one ear at a time, by using headphones (HDA200, manufactured by SENNHEISER). The sound pressure of each sound stimulation was subjected to calibration by using a noise level meter (LA-1440 from ONO SOKKI) and a coupler (IEC318 from Larson Davis).

FIG. 2A schematically shows the sound stimulations presented in Electroencephalogram measurement experiment 1, and FIG. 2B schematically shows the sound stimulations in Electroencephalogram measurement experiment 2.

Prior to each experiment, it was explained to the participants that no attention needed to be paid to the sound stimulations.

The interval between sound stimulations within the sound stimulation group (i.e., ISI1 in FIGS. 2A and 2B) was fixed at 300 ms. The interval between sound stimulation groups (i.e., ISI2 in FIGS. 2A and 2B) was randomly decided in a range of 450±50 ms. In each block, the sound stimulation group was repeated 20 times for each of the right or left ear and for each frequency (resulting in the sound stimulation group being repeated a total of 160 times). For an improved measurement accuracy, 3 blocks to 5 blocks of sound stimulation group presentation were performed.

When a sound stimulation group of the same frequency is successively presented to the same ear, the participant may become accustomed to the sound stimulations, thus resulting in a small event-related potential amplitude. This phenomenon is called the taming (habituation) of auditory evoked potential. In order to reduce taming of auditory evoked potential, the frequency and the ear for which to present the sound stimulation group were determined under the following constraints.

A sound stimulation group of a different frequency from that of an immediately previous sound stimulation group is presented, and no sound stimulation group of the same frequency is successively presented.

The ear to which the sound stimulation group is presented is randomly selected between right and left. However, in order to ensure randomness of stimulations to the right or left ear, not more than four sound stimulation groups are successively presented to either the right or left ear.

Figure 3A:
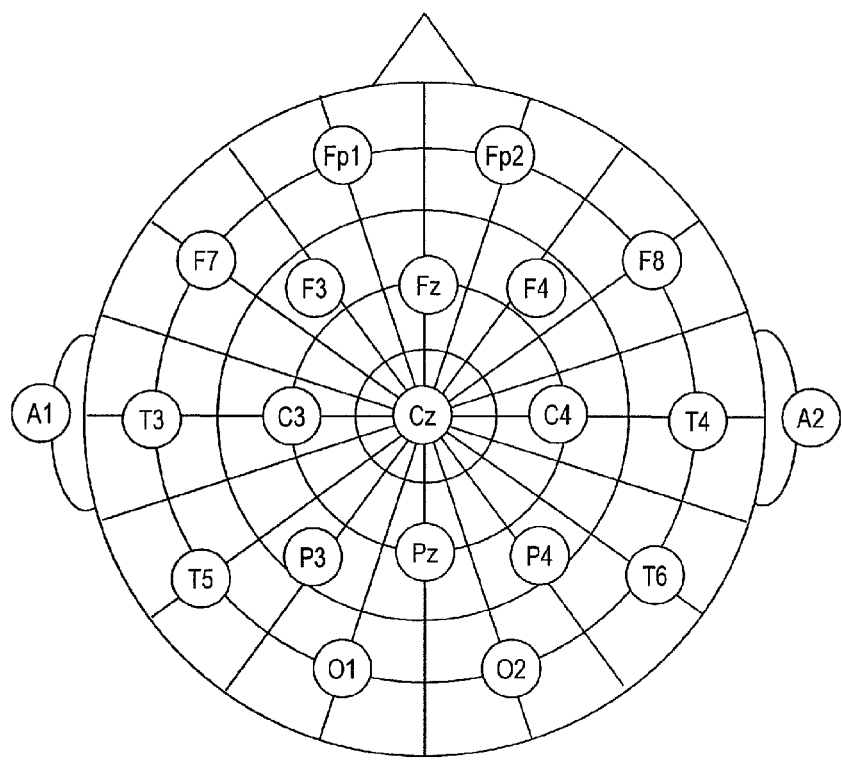
FIGS. 3A and 3B are diagrams showing electrode positions according to the International 10-20 system, and electrode positions in an electroencephalographic experiment conducted by the inventors.
Figure 3B:
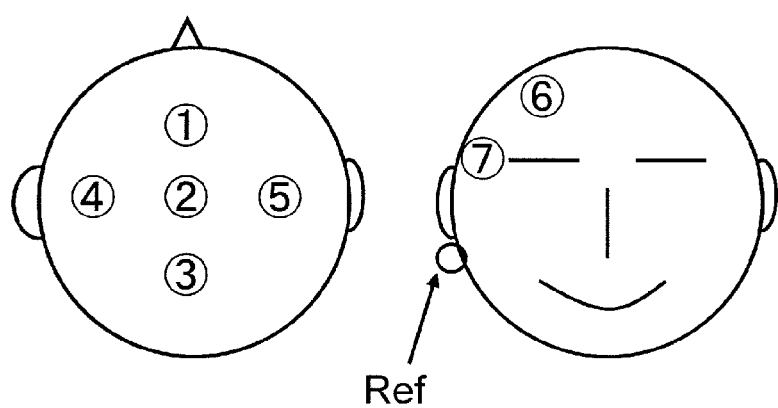

Next, the positions of electrodes to be worn for electroencephalogram measurement will be described. FIG. 3A shows electrode positions according to the International 10-20 system (10-20 System). FIG. 3B shows the positions of electrodes worn in this experiment. In FIG. 3B, circled numbers 1 to 5 represent electrode positions Fz, Cz, Pz, C3, and C4, respectively.

The inventors measured as the electroencephalogram potential differences between active electrodes worn at Fz, Cz, Pz, C3, and C4 and a reference electrode worn at the right mastoid. A "mastoid" is a protrusion of the cranium below the hind root of an ear. FIG. 3B shows the mastoid position as "Ref".

Moreover, in order to measure electrooculographic noises that would mix into the electroencephalogram through blinks and eye movements, electrodes (circled numbers 6 and 7 in FIG. 3B) were placed above the right eye and to the right of the right eye.

The sampling frequency was 1000 Hz, and the time constant was 1 second. A 30 Hz analog low-pass filter was applied.

A 1-20 Hz digital band-pass filter was applied over the entire duration of electroencephalogram data which was measured off-line. Thereafter, as an event-related potential in response to a sound stimulation for each of the right or left ear, each frequency, and each sound pressure, a waveform from −100 ms to 1000 ms was cut out from the first sound of each sound stimulation group as a starting point. As used herein, "−100 ms" means a point in time which is 100 milliseconds before the point in time of presenting the first sound.

Moreover, a continuous wavelet transform was performed for an electroencephalogram waveform in the range from 0 ms to 900 ms of the event-related potential, and a wavelet coefficient for each time and each frequency was obtained. As the mother wavelet, the Mexican hat function ($\phi(t)=(1-t^2)\exp(-t^2/2)$) was used. The wavelet transform is a method of determining time-frequency components of event-related potential. So long as time-frequency components are obtained, a short-time Fourier transform may be performed, for example, without being limited to the wavelet transform.

Arithmetic means of the waveform and wavelet coefficient of event-related potential were taken for each individual, each of the right or left ear, and each frequency. These are respectively referred to as an arithmetic mean waveform and an arithmetic mean wavelet coefficient. Those trials which exhibited an amplitude with an absolute value of 80 μV or more at any electrode were excluded from the total arithmetic mean and arithmetic mean, because they presumably were under influence of noises, e.g., eye movements and blinks.

As a characteristic amount extracted from event-related potential that can serve as an index of hearing aid gain, a wavelet characteristic amount was derived. As used herein, a wavelet characteristic amount is obtained as an average value taken, in each of e.g. 30 divided parts along the time axis (every 30 ms) and each of e.g. 9 divided parts along the frequency axis (e.g. from 2.5 Hz to 12.5 Hz), of an arithmetic mean wavelet coefficient.

Hereinafter, results of the electroencephalogram measurement experiment will be described.

First, in order to confirm that an index of hearing aid gain is contained in the event-related potential in response to changing sound pressures, an actual hearing aid gain under a 90 dBSPL input or a 80 dB input measured in the hearing aid characteristics measuring experiment was compared against an arithmetic-meaned event-related potential which was obtained in the electroencephalogram measurement experiment. In order to estimate a hearing aid gain from the event-related potential, it is essential that a difference in event-related potential exists that reflects the hearing aid gain of each participant.

Based on the magnitude of hearing aid gain as measured in the hearing aid characteristics measuring experiment, the experimental participants were divided into two groups. More specifically, for each frequency, a group with a large hearing aid gain (hearing aid output) and a group with a small hearing aid gain were established, depending on whether the hearing aid output under a 90 dBSPL input or a 80 dBSPL input was equal to or greater than the average value, or smaller than the average value.

Figure 4A:
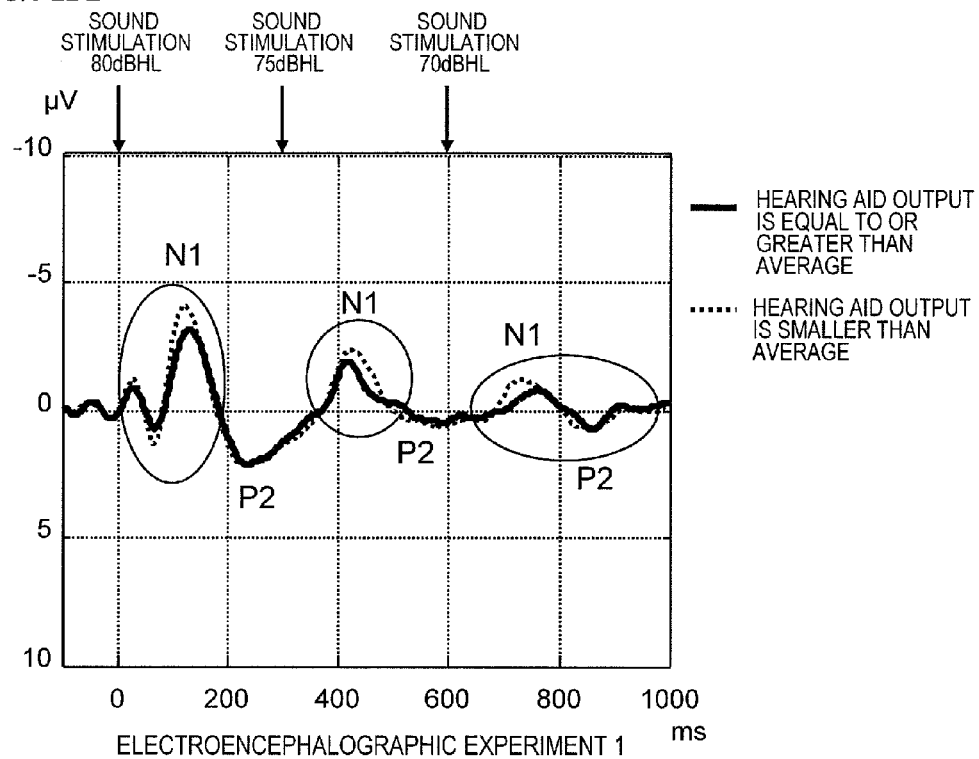
FIGS. 4A and 4B show graphs showing exemplary characteristic data of event-related potential in an electroencephalographic experiment conducted by the inventors.
Figure 4B:
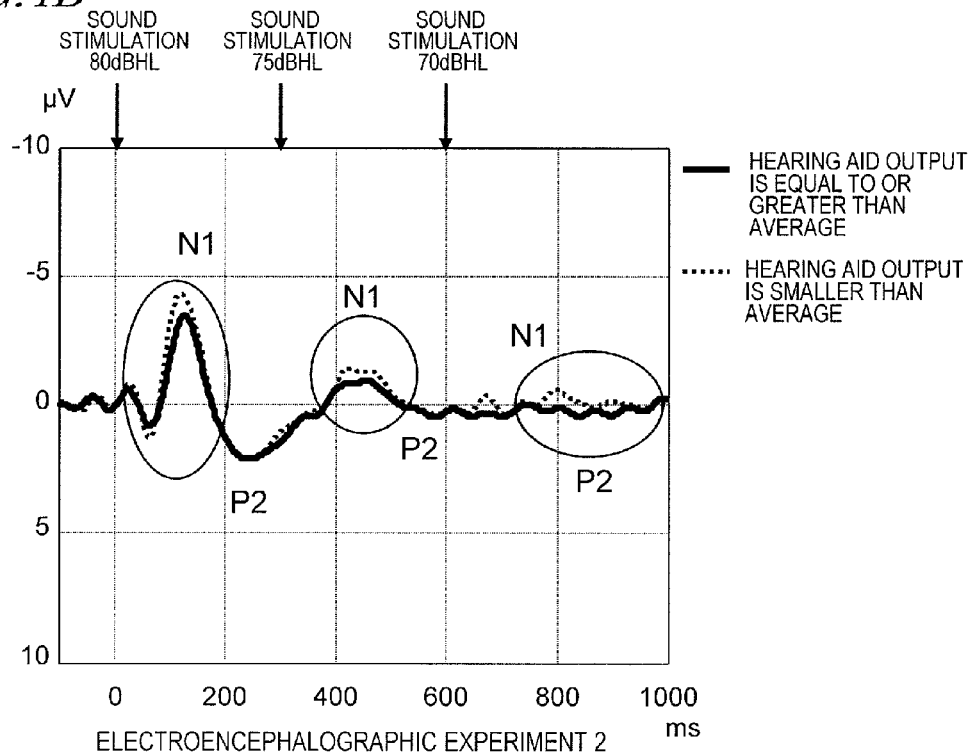

FIG. 4A and FIG. 4B show arithmetic mean waveforms at the central portion (Cz) in Electroencephalogram measurement experiment 1 and Electroencephalogram measurement experiment 2. Each solid line represents the group whose hearing aid output is equal to or greater than the average, while each broken line represents the group whose hearing aid output is smaller than the average. The horizontal axis represents time in units of ms, and the vertical axis represents potential in units of μV. On the horizontal axis, 0 ms indicates the point in time of presenting the first sound.

A negative component which appears at about 100 ms since the timing of each sound stimulation presentation indicated by an arrow is an N1 component. A positive component which appears at about 200 ms since the timing of each sound stimulation presentation indicated by an arrow is a P2 component. Regardless of whether the output sound from the hearing aid is large or small, an N1 component and a P2 component appear.

It can also be seen that the N1 component of the event-related potential corresponding to the group with a small hearing aid output (broken line) is greater in amplitude than the N1 component of the event-related potential corresponding to the group with a large hearing aid output (solid line).

Note that these results are dissimilar from the waveforms of arithmetic mean event-related potentials when the same sound stimulations are presented to people with normal hearing, who are then grouped based on their subjectively-reported UCL evaluation (called "subjective UCL") being large or small. Relative to the people with normal hearing that had a large subjective UCL, the people with normal hearing that had a small subjective UCL exhibited a P2 component with a small amplitude, especially in response to the second sound and third sound. In other words, while there may be differences in hearing among participants, it is presumably in a different form from an index of UCL that an index of hearing aid output under a 90 dBSPL input appears in the event-related potential waveform.

Figure 5:
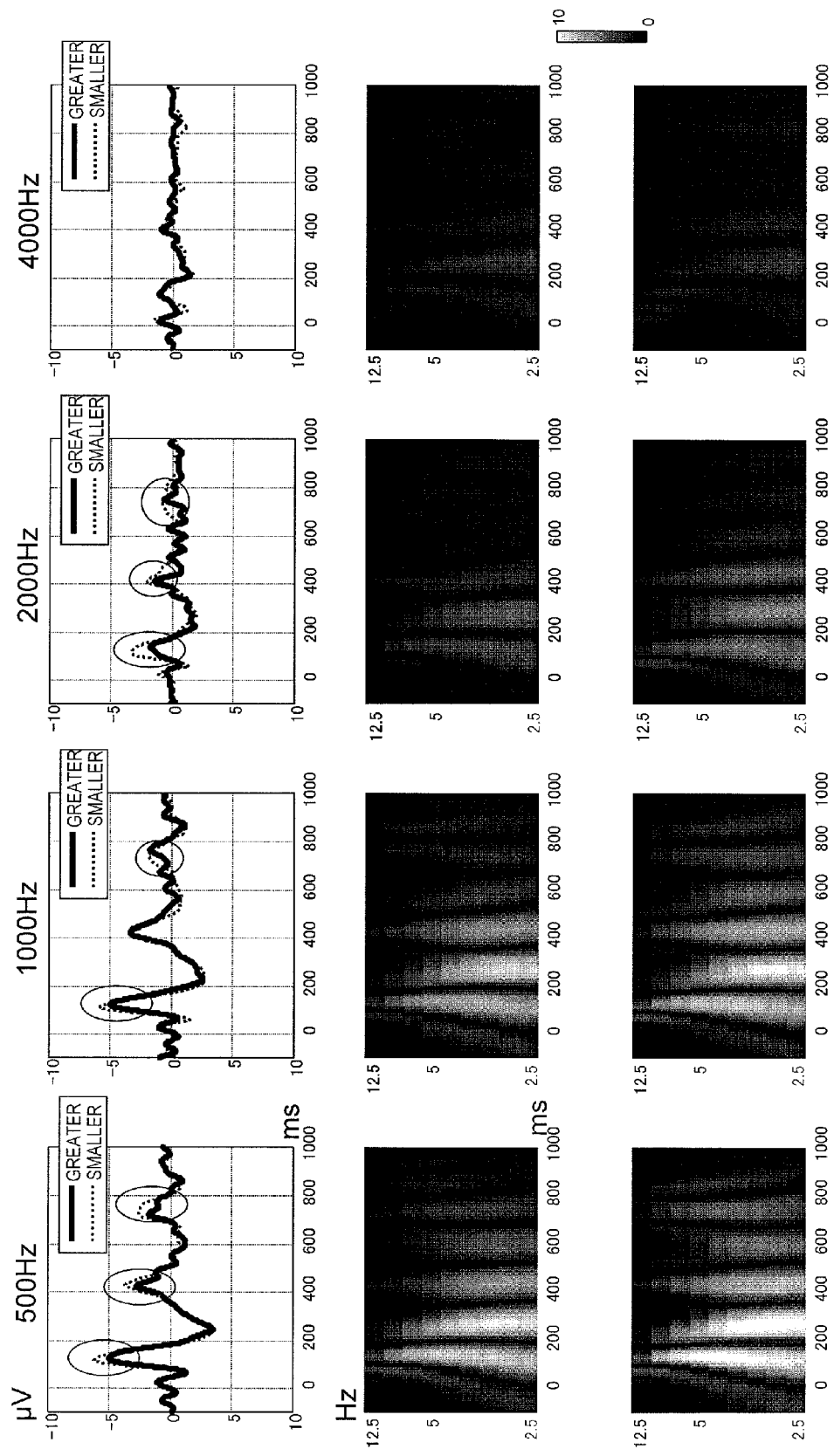
FIG. 5 shows graphs showing exemplary arithmetic mean waveforms and wavelet coefficients for different frequencies, in Electroencephalogram measurement experiment 1 conducted by the inventors.
Figure 6A:
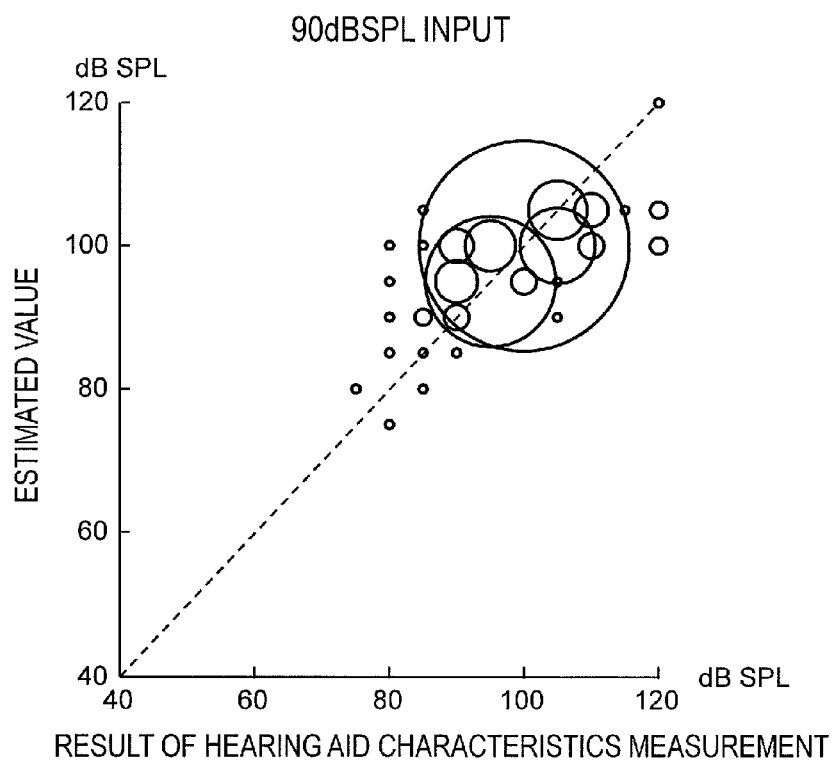
FIGS. 6A and 6B are graphs showing fluctuations in hearing aid outputs for a 90 dBSPL input and a 80 dBSPL input obtained in a hearing aid characteristics measuring experiment and results of hearing aid output estimation as estimated from Electroencephalogram measurement experiment 1.
Figure 6B:
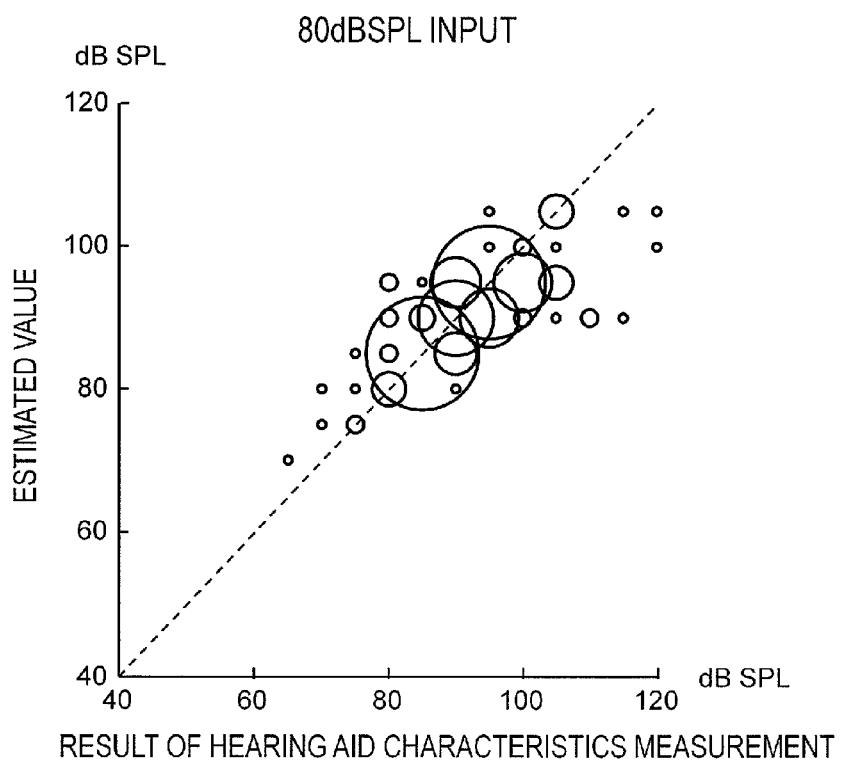
Figure 13:
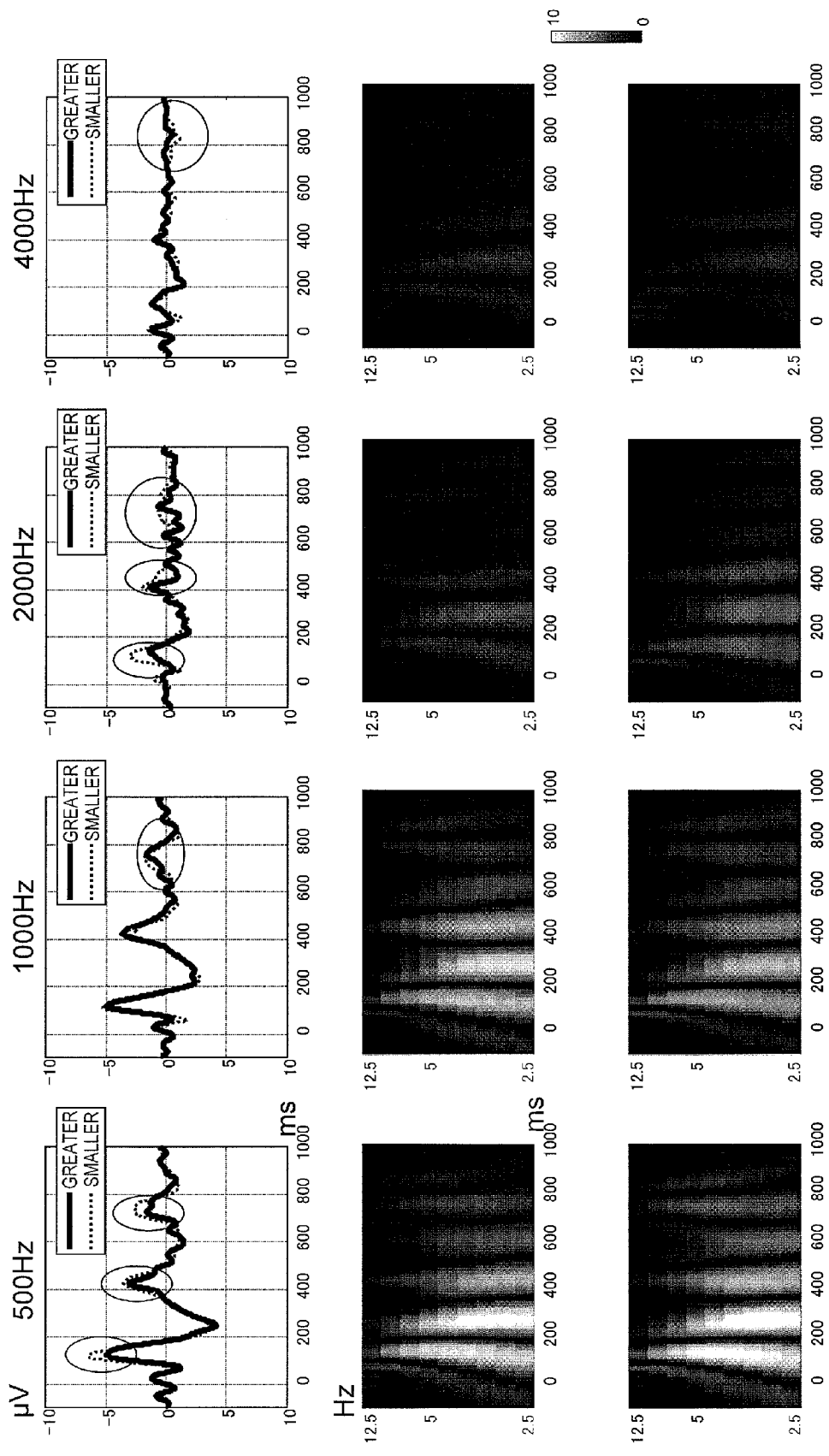
FIG. 13 shows graphs showing exemplary arithmetic mean waveforms and wavelet coefficients for different frequencies, in Electroencephalogram measurement experiment 2 conducted by the inventors.
Figure 14A:
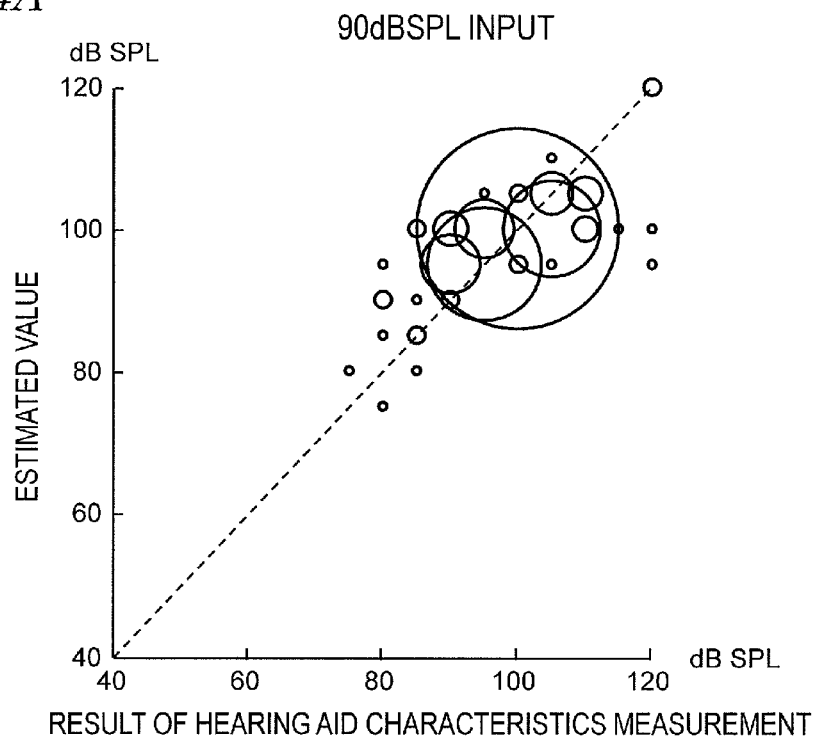
FIGS. 14A and 14B are graphs showing fluctuations in hearing aid outputs for a 90 dBSPL input and a 80 dBSPL input obtained in a hearing aid characteristics measuring experiment and results of hearing aid output estimation as estimated from Electroencephalogram measurement experiment 2.
Figure 14B:
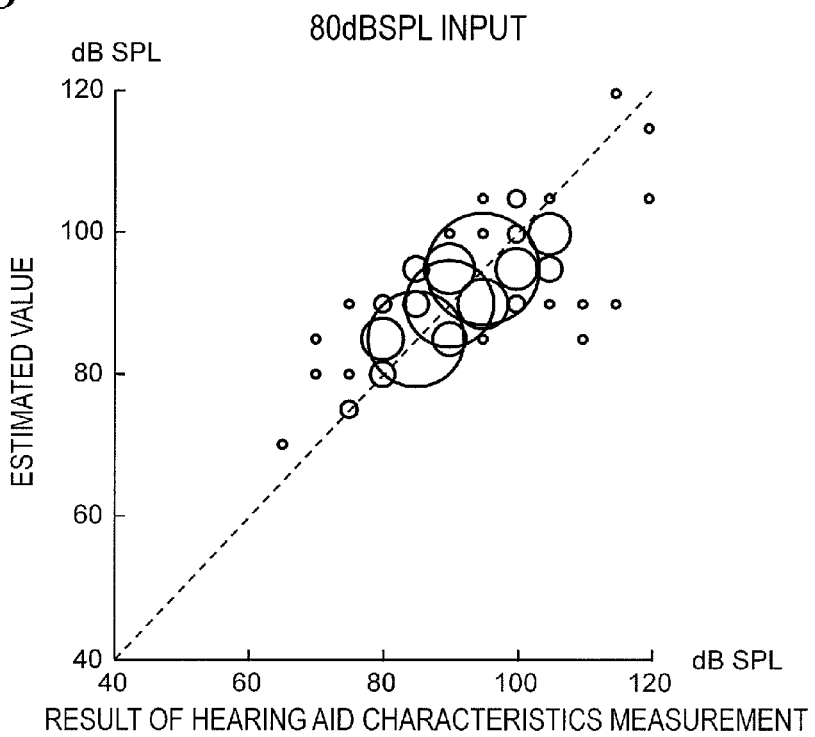

FIG. 5 and FIG. 13 show arithmetic mean waveforms and arithmetic mean wavelet coefficients for different input sound frequencies (500, 1000, 2000, 4000 Hz) in Electroencephalogram measurement experiment 1 and Electroencephalogram measurement experiment 2. In the upper row of FIG. 5 is shown arithmetic mean waveforms; in the middle row is shown arithmetic mean wavelet coefficients in the cases where the hearing aid output is equal to or greater than the average; and in the lower row is shown arithmetic mean wavelet coefficients in the cases where the hearing aid output is smaller than the average.

Similarly to FIGS. 4A and 4B, each solid line represents the case where the hearing aid output is equal to or greater than the average, and each broken line represents the case where it is smaller than the average. The horizontal axis represents time in units of ms, and the vertical axis represents potential in units of V. On the horizontal axis, 0 ms indicates the point in time of presenting the first sound. It can be seen that, although the absolute value of the amplitude of the N1 component differs depending on frequency, the N1 component amplitude is greater when the hearing aid output is smaller-than-average than when the hearing aid output is equal to or greater than the average. It can also be seen that, at the arithmetic mean wavelet coefficients in the time slots of particular difference in arithmetic mean, there is a difference depending on the hearing aid output being large or small.

2-4. Estimation of Hearing Aid Output

From the results of Electroencephalogram measurement experiment 1 and Electroencephalogram measurement experiment 2, it was examined whether results of hearing aid characteristics measurement under a 90 dBSPL input and under a 80 dBSPL input are estimatable. Linear discrimination was used for the hearing aid output estimation. As described earlier, a hearing aid gain is obtained by subtracting an input sound pressure from the output sound pressure of a hearing aid. Therefore, once the hearing aid output is estimated, it can be said that the hearing aid gain has also been estimated.

First, a wavelet characteristic amount was determined, as described above. The wavelet characteristic amount was generated by taking an average of the arithmetic mean wavelet coefficients for every scale (frequency range) over a range of 0 to 900 ms, in time windows of 50 ms. Next, in order to make an estimation based on linear discrimination, hearing aid outputs under a 90 dBSPL input and under a 80 dBSPL input that were measured in the hearing aid characteristics measuring experiment were rounded to every 5 dB. Thus, the hearing aid characteristics in every 5 dB steps were estimated through linear discrimination.

Specifically, each measured hearing aid output was rounded up on 2 and down on 3. Then, two arbitrary wavelet characteristic amounts were combined, and the correspondence between the hearing aid outputs in every 5 dB steps and wavelet characteristic amounts of participants other than oneself was used as training data. The training data was generated for each stimulation frequency, from pooled data of the right and left ears for each input sound pressure.

The accuracy of hearing aid output estimation was evaluated in terms of average error (i.e., an average of the absolute values of differences between hearing aid outputs of all participants for each of the right or left ear and each frequency, taken in every 5 dB steps, and the estimated hearing aid outputs). The average error was calculated for all wavelet characteristic amount combinations.

FIGS. 6A, 6B and FIGS. 14A, 14B indicate results of conducting linear discrimination based on the wavelet characteristic amounts obtained through, respectively, Electroencephalogram measurement experiment 1 and Electroencephalogram measurement experiment 2. As an indication of linear discrimination results, a distribution of correspondence between hearing aid outputs for a 90 dBSPL input or a 80 dBSPL input measured in the hearing aid characteristics measuring experiment and the estimated hearing aid outputs obtained through discriminant analysis by using the wavelet characteristic amounts is each shown, where pooled data of the right and left ears and stimulation frequencies is used. At each lattice point, frequency is indicated by a circle symbol in a corresponding size. Any circle symbol whose center is on the broken line indicates a case where the hearing aid output was correctly estimated.

It can be seen that, under both experiments and both input sound pressures, hearing aid outputs are being successfully estimated from the measured electroencephalogram, despite some fluctuations. The average errors in hearing aid output estimation for a 90 dBSPL input and a 80 dBSPL input in Electroencephalogram measurement experiment 1 were, respectively, 4.6 dB and 5.1 dB. The average errors in hearing aid output estimation for a 90 dBSPL input and a 80 dBSPL input in Electroencephalogram measurement experiment 2 were, respectively, 4.6 dB and 5.2 dB. Thus it can be said that, from the event-related potentials measured while successively presenting three pure tones of the same frequency with a decrement of every 5 dB or 15 dB from 80 dBHL, a hearing aid output for each frequency, under a 90 dBSPL input or a 80 dBSPL input, can be estimated with a high precision.

Incidentally, as the inventors confirmed, estimating hearing aid outputs by using the aforementioned wavelet characteristic amount with respect to input sounds having sound pressures of 60 dBSPL and 70 dBSPL resulted in a lower accuracy of estimation. Therefore, the above-described hearing aid output estimation utilizing electroencephalogram may be performed for estimating a hearing aid output with respect to an input sound pressure of 80 dBSPL or more.

In order to examine which time slot and frequency band produce a wavelet characteristic amount that most characteristically contains information related to hearing aid output estimation, a distribution of wavelet characteristic amounts that minimize the average error was examined. FIG. 7 shows a result from Electroencephalogram measurement experiment 1, whereas FIG. 15 shows a result from of Electroencephalogram measurement experiment 2. In the upper rows of FIG. 7 and FIG. 15 is shown the occurrence frequency of wavelet characteristic amounts used in the upper 1% estimations exhibiting least average errors. Both results indicate that the average error becomes small when using wavelet coefficients in a time slot near the N1 component (latency of about 100 ms) in response to the first sound, a time slot near the P2 component (latency of about 200 ms) in response to the second sound, and a time slot near the P2 component in response to the third sound.

The lower rows of FIG. 7 and FIG. 15 indicate the occurrence frequency of wavelet characteristic amounts in every time window of 50 ms (six time windows for each of the first to third sounds) used in the upper 1% estimations. Both results indicate that the average error becomes small when using wavelet coefficients in a time slot near the N1 component (latency of about 100 ms) in response to the first sound, a time slot near the P2 component (latency of about 200 ms) in response to the second sound, and a time slot near the P2 component in response to the third sound. Among the upper 1% estimations, what was utilized across most results commonly with a probability of 15% or more was wavelet characteristic amounts in a time slot near the N1 component in response to the first sound, a time slot near the P2 component in response to the second sound, time slots near the N1 component and P2 component in response to the third sound.

Note that discriminant analysis may be conducted with not only the wavelet characteristic amount, but also with the information of P1-N1 amplitude and N1-2 amplitude.

Thus, it has become clear through the subjective report experiment and electroencephalogram measurement experiments conducted by the inventors that, when three pure tones of the same frequency with monotonously descending sound pressures are presented in a sound pressure range that is lower than a sound pressure which is generally evaluated to be the UCL, a hearing aid output under a 90 dBSPL input or a 80 dBSPL input, for example, can be estimated by using a characteristic amount (e.g., wavelet-coefficient related characteristic amount) contained in the electroencephalogram in response to each sound stimulation from first to third sounds.

Embodiment 1

Hereinafter, first, the hearing aid gain determination system 100 will be described in outline. Thereafter, the construction and operation of a hearing aid gain determination system 100 including the hearing aid gain measurement apparatus 1 will be described.

The hearing aid gain determination system 100 according to the present embodiment measures an electroencephalogram (event-related potential) of a user to whom a sound stimulation is presented, extracts a characteristic amount therefrom, and from a change pattern of the characteristic amount, determines a hearing aid gain under: (1) a 90 dBSPL input or a 80 dBSPL input; or (2) a 90 dBSPL input and a 80 dBSPL input.

In the present embodiment, a probe electrode is provided at the central portion (Cz), and a reference electrode is provided on the right mastoid, thus to measure an electroencephalogram as a potential difference between the probe electrode and the reference electrode. There is a possibility that the level and polarity of a characteristic component of the event-related potential may vary depending on the position at which the electrode for electroencephalogram measurement is attached, and the positions at which the reference electrode and the probe electrode are set. However, based on the following description, those skilled in the art will be able to make appropriate modifications so as to adapt to the particular positions of the reference electrode and the probe electrode, extract a characteristic feature of event-related potential, and measure an uncomfortable sound pressure. Such variants are within the scope of the present invention.

FIG. 8 shows the functional block construction of a hearing aid gain determination system 100 (hereinafter referred to as a gain determination system 100) according to the present embodiment. The gain determination system 100 includes a sound stimulation output section 10, a biological signal measurement section 50, and a hearing aid gain determination apparatus 1 (which hereinafter may also be referred to as the gain determination apparatus 1).

The gain determination apparatus 1 includes an event-related potential characteristic amount extraction section 55, a hearing aid gain determination section 65, a sound stimulation group determination section 70, a sound stimulation sound pressure determination section 71, a sound stimulation generation section 75, and a hearing aid gain setting section 80. In the following, the event-related potential characteristic amount extraction section 55 may be referred to as the "characteristic amount extraction section 55"; the hearing aid gain determination section 65 as the "gain determination section 65"; the sound stimulation sound pressure determination section 71 as the "sound pressure determination section 71"; and the hearing aid gain setting section 80 as the "gain setting section 80".

The gain determination apparatus 1 is connected to the sound stimulation output section 10 and the biological signal measurement section 50 in a wired or wireless manner. The sound stimulation output section 10 is constructed so as to present sound stimulations to the user 5, whereas the biological signal measurement section 50 is constructed so as to measure a biological signal (electroencephalogram) of the user 5. For conciseness of explanation, the user 5 block is also shown in the figure.

The sound stimulation output section 10 outputs to the user 5 a sound stimulation group (first sound, second sound, and third sound) of a certain frequency, with monotonously descending sound pressures in a sound pressure range that is lower than a sound pressure which is generally evaluated to be the UCL.

The biological signal measurement section 50 is connected to at least two electrodes A and B. For example, electrode A is attached to a mastoid of the user 5, whereas electrode B is attached at the central portion (so called Cz) on the scalp of the user 5. The biological signal measurement section 50 measures an electroencephalogram of the user 5 corresponding to a potential difference between electrode A and electrode B.

From the electroencephalogram (event-related potential) of the user 5 measured from the point of presenting each of the first to third sounds as a starting point, the gain determination apparatus 1 extracts a wavelet coefficient containing time-frequency information as a characteristic amount. By using the extracted characteristic amounts in response to the first to third sounds, the gain determination apparatus 1 estimates a hearing aid gain of the user 5. Each component element will be specifically described later.

<Environment of Use>

Figure 9:
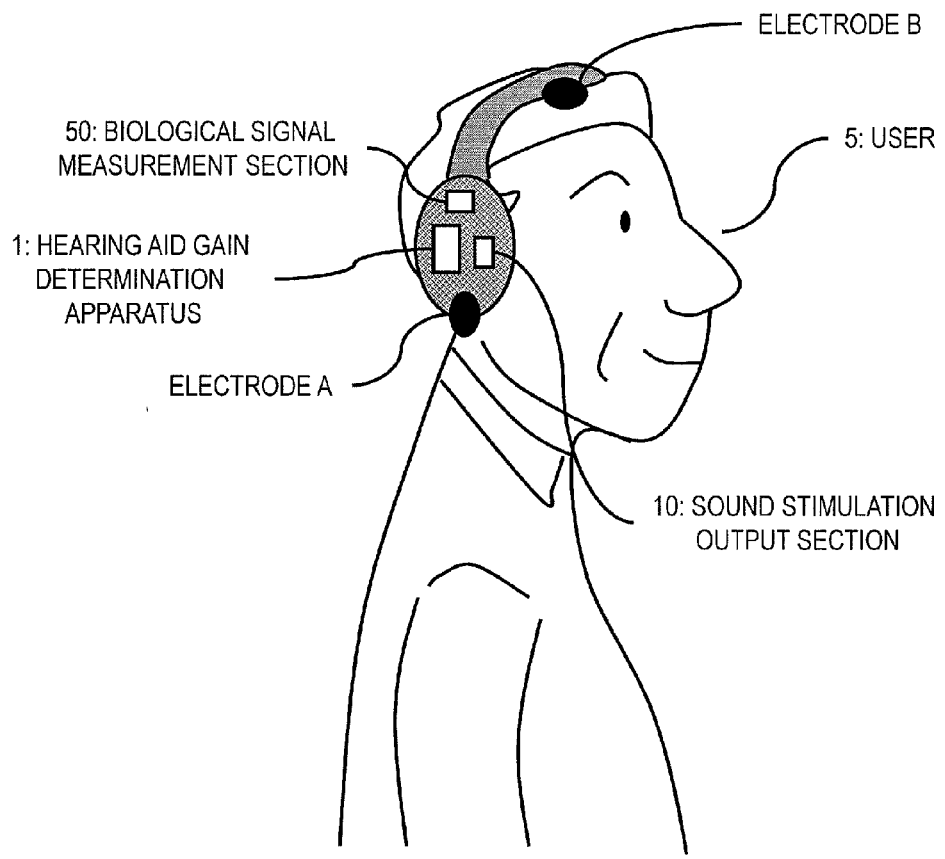
FIG. 9 is a diagram showing an exemplary environment of use for the hearing aid gain determination system.

FIG. 9 shows the construction and environment of use of the hearing aid gain determination system 100 according to the present embodiment. The gain determination system 100 corresponds to the system construction of Embodiment 1 shown in FIG. 8.

Thus, the hearing aid gain determination system 100 includes the gain determination apparatus 1, the sound stimulation output section 10, and the biological signal measurement section 50.

The biological signal measurement section 50 and the sound stimulation output section 10 of the gain determination system 100 may be accommodated in the same housing. Alternatively, the biological signal measurement section 50 and the sound stimulation output section 10 of the gain determination system 100 may be accommodated in a separate housing. In that case, the biological signal measurement section 50 sends a measured electroencephalogram signal to the gain determination apparatus 1 being connected in a wireless or wired manner.

The gain determination apparatus 1 determines information of sound stimulations for hearing aid gain measurement. The sound stimulation information may include, for example, the ear to which the stimulation is presented (right or left ear), sound frequency, sound pressure, and timing of sound presentation. The sound stimulation output section 10 presents to the user 5 the sound stimulations thus determined by the gain determination apparatus 1.

Moreover, from the event-related potential cut out based on each sound stimulation of the first to third sounds as a starting point, the gain determination apparatus 1 extracts a characteristic amount with which to estimate a hearing aid output.

For example, in the case where the sound pressure of a sound which is output from a hearing aid is adjustable, the gain determination system 100 of the present embodiment estimates the hearing aid gain at a volume which is daily used by the user. "Volume" means an amount by which a hearing aid applies universal amplification to every sound.

For example, a hearing aid gain under an input sound pressure of 90 dBSPL is estimated. The output sound pressure of a hearing aid under an input sound pressure of 90 dBSPL is important for determining the compression ratio of a hearing aid of non-linear amplification type (Kazuoki KODERA, "HOCHOKI FITTINGU NO KANGAEKATA (or "Concept of Hearing Aid Fitting"), 3rd edit., p. 81).

In order to determine a compression ratio more accurately, it is preferable to determine not only an output sound pressure of the hearing aid under an input sound pressure of 90 dBSPL, but also an output sound pressure of the hearing aid under an input sound pressure other than 90 dBSPL.

For example, based on a pattern of changing characteristic amounts with respect to changing sound pressures, a hearing aid output is determined for each of the right or left ear, and for each frequency, under: (1) 90 dBSPL input or a 80 dBSPL input; or (2) a 90 dBSPL input and a 80 dBSPL input.

<Hardware Construction of Hearing Aid Gain Determination Apparatus 1>

Figure 10:
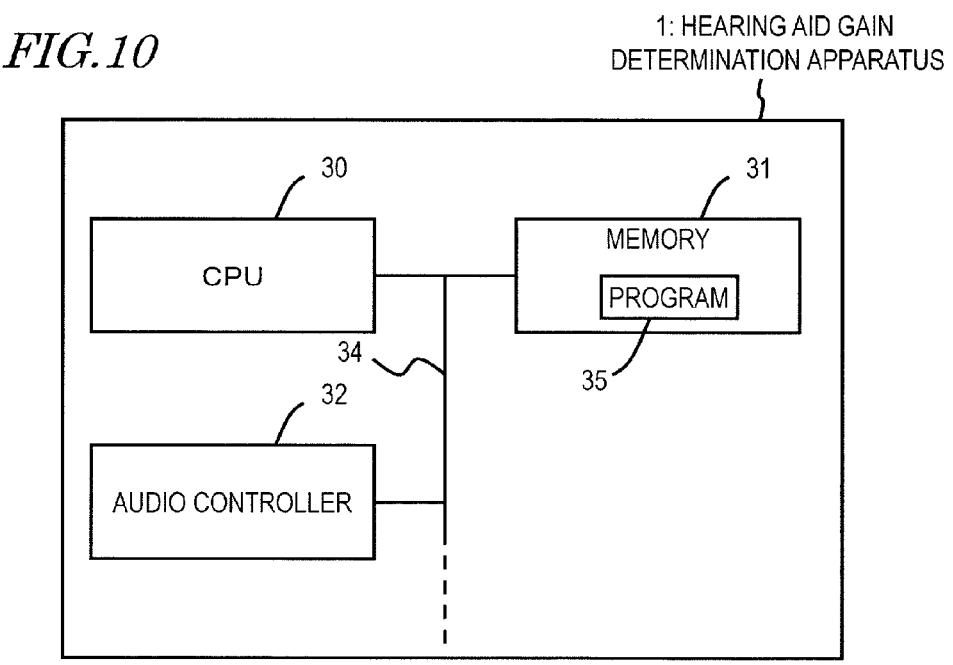
FIG. 10 is a diagram showing an exemplary hardware construction according to Embodiment 1.

FIG. 10 shows the hardware construction of the hearing aid gain determination apparatus 1 according to the present embodiment. The gain determination apparatus 1 includes a CPU 30, a memory 31, and an audio controller 32. The CPU 30, the memory 31, and the audio controller 32 are interconnected via a bus 34, so that data exchange among them is possible.

The CPU 30 executes a computer program 35 which is stored in the memory 31. A processing procedure as illustrated by a subsequently-described flowchart is described in the computer program 35.

In accordance with the computer program 35, the gain determination apparatus 1 performs processes such as generation of sound stimulations, characteristic amount extraction from event-related potential, and discriminant analysis for hearing aid gain determination. These processes will be specifically described later.

In accordance with instructions from the CPU 30, the audio controller 32 outputs the sound stimulations for presentation via the sound stimulation output section 10 at designated sound pressures.

Note that the gain determination apparatus 1 may be implemented as a piece of hardware (e.g., a DSP) consisting of a semiconductor circuit having a computer program incorporated therein. Such a DSP can realize all functions of the aforementioned CPU 30, memory 31, and audio controller on a single integrated circuit. For example, the characteristic amount extraction section 55, the gain determination section 65, the sound stimulation group determination section 70, the sound pressure determination section 71, the sound stimulation generation section 75, and the gain setting section 80 are realized by the CPU 30.

The aforementioned computer program 35 may be distributed on the market in the form of a product recorded on a storage medium such as a CD-ROM, or transmitted through telecommunication lines such as the Internet. Upon reading the computer program 35, a device having the hardware shown in FIG. 10 (e.g., a PC) is able to function as the gain determination apparatus 1 according to the present embodiment.

The respective functional blocks of the gain determination apparatus 1 correspond to functions which are realized by the CPU 30, the memory 31, and the audio controller 32 as a whole upon executing the program which has been described in conjunction with FIG. 10.

Hereinafter, the respectively component elements of the hearing aid gain determination system 100 will be described.

<Sound Stimulation Group Determination Section 70>

The sound stimulation group determination section determines information of a plurality of sound stimulations (sound stimulation group) to be presented to the user 5. In the present embodiment, the sound stimulation group at least includes a first sound, a second sound, and a third sound.

The sound stimulation group information includes, for example, the ear to which a sound stimulation is presented (right ear or left ear), the frequency of the presented sound stimulation, the duration of each sound stimulation in the sound stimulation group, and the interval between sound stimulations. The sound stimulation group information may at least include the sound stimulation frequency and the interval between sound stimulations. Note that, rather than being determined by the sound stimulation group determination section 70, the interval between sound stimulations may be governed by predetermined information which is stored in the sound stimulation output section 10 described later.

It is desirable that any sound presented by the gain determination system 100 has a sound pressure of a level which is not felt uncomfortable to the user. Such sound pressure control may be performed by the sound pressure determination section 71 described later, for example.

The ear and frequency for presentation of the sound stimulation group may be randomly determined based on the following constraints, for example. No sound stimulation of the same frequency as the immediately previous sound stimulation group is selected. The ear is preferably selected in random order between right and left. However, it is preferable that not more than four sound stimulation groups are successively presented to either the right or left ear. Thus, the influence of taming (habituation) of the electroencephalogram due to successive presentation of sound stimulation groups to the same ear and with the same frequency is reduced, whereby hearing aid gain measurement can be realized with a high precision. The duration of a sound stimulation may be set to e.g. 25 ms or more, so that an auditory evoked potential will be stably induced. Moreover, the interval between stimulations is set to a time which is equal to or greater than the duration of a sound stimulation and equal to or less than 1 second, e.g., 300 ms or 200 ms.

<Sound Stimulation Sound Pressure Determination Section 71>

The sound pressure determination section 71 receives sound stimulation group information from the sound stimulation group determination section 70.

The sound stimulation group information is, for example, the ear to which a sound stimulation is presented (right ear or left ear), the frequency of the presented sound stimulation, the duration of each sound stimulation in the sound stimulation group, and the interval between sound stimulations.

It suffices if the first sound, the second sound, and the third sound at least have the same frequency. "Same frequency" is inclusive of sounds with a frequency difference that is smaller than is aurally distinguishable to humans. In the present specification, frequencies with a difference of 5 Hz or less are regarded as the same frequency.

The sound pressure determination section 71 determines the sound pressures of the first to third sounds in the sound stimulation group to be in a sound pressure range which is lower than a given predetermined threshold value. Moreover, in the present embodiment, the sound pressure determination section 71 determines the sound pressures of the first to third sounds so that the respective sounds consecutively decrease in sound pressure, i.e., so as to satisfy the relationship: sound pressure of first sound>sound pressure of second sound>sound pressure of third sound.

Herein, the predetermined threshold value may be a sound pressure which is generally evaluated to be the UCL, for example. In other words, the sound pressures of the first to third sounds are determined so as to fall within a sound pressure range that is comfortably heard to the user 5.

The sound stimulation sound pressure determination section 71 may retain a predetermined threshold value in advance. The sound stimulation sound pressure determination section 71 may determine the sound pressure of the first sound to be 80 dBHL, the sound pressure of the second sound to be 75 dBHL, and the sound pressure of the third sound to be 70 dBHL, for example, so that they are all below this threshold value. Alternatively, for example, the sound pressure of the first sound may be determined to be 80 dBHL, the sound pressure of the second sound to be 65 dBHL, and the sound pressure of the third sound to be 50 dBHL.

Moreover, the sound stimulation sound pressure determination section 71 may be controlled so as to never select any sound pressure that is greater than the predetermined threshold value.

<Sound Stimulation Generation Section 75>

Based on the sound stimulation group information received from the sound pressure determination section 71, the sound stimulation generation section 75 generates sound stimulation data. Each sound stimulation may be a tone burst sound having a rise and fall of 3 ms, for example.

The sound stimulation generation section 75 outputs a sound stimulation to the user 5 via the sound stimulation output section 10, and outputs a trigger signal to the biological signal measurement section 50 at that timing. Note that the sound stimulation generation section 75 may be arranged so as to only have a function of sending generated sound stimulation data to the sound stimulation output section 10.

The sound stimulation data may be generated in such a manner that a single piece of sound stimulation data is created for one sound stimulation group, from which a plurality of sound stimulations that undergo changes in sound pressure at a predetermined time interval are derived, for example. In that case, the trigger signal to be sent to the biological signal measurement section 50 may only be sent at the timing of presenting the first sound.

Note that the sound stimulation generation section may include an input device, or be connected to an external input device. In this case, the user 5 or a person who tests the hearing of the user 5 is able to input desired information concerning sound stimulations by using the input device, and the sound stimulation generation section 75 can generate sound stimulations by using the information received from the input device.

<Sound Stimulation Output Section 10>

In accordance with the sound stimulation data generated by the sound stimulation generation section 75, the sound stimulation output section 10 presents sounds to the user 5. Preferably, the sound stimulation output section 10 correctly outputs sound stimulations generated by the sound stimulation generation section 75 to the right or left ear. The sound stimulation output section 10 may include headphones or a loudspeaker whose frequency characteristics are free of distortion, for example.

<Biological Signal Measurement Section 50>

The biological signal measurement section 50 is a measuring instrument for measuring a biological signal of the user 5. In the present disclosure, the biological signal measurement section 50 is an electroencephalograph. As the biological signal, the biological signal measurement section measures an electroencephalogram corresponding to a potential difference between a probe electrode and a reference electrode worn by the user 5.

The measured electroencephalogram may be subjected to frequency filtering with an appropriate cutoff frequency. The biological signal measurement section 50 sends the measured electroencephalogram or filtered electroencephalogram to the event-related potential characteristic amount extraction section 55. Hereinafter, a measured or filtered electroencephalogram may also be referred to as "electroencephalogram data".

For example, the biological signal measurement section 50 may be arranged to apply frequency filtering with an appropriate cutoff frequency to the electroencephalogram data, cut out an event-related potential in a predetermined zone (e.g., a zone from 100 ms before the first sound presentation to 400 ms after the third sound presentation) based on the trigger signal received from the sound stimulation generation section 75 as a starting point, and send that waveform data (event-related potential) to the event-related potential characteristic amount extraction section 55.

In the case where a band-pass filter is used as the frequency filter, the cutoff frequency may be set so as to pass e.g. 1 Hz to 20 Hz. It is assumed that the user 5 has worn the electroencephalograph in advance. The probe electrode for electroencephalogram measurement is attached at the central portion Cz, and the reference electrode is attached at the mastoid, for example.

The electroencephalogram data contains event-related potential. The event-related potential is a change in the potential of an electroencephalogram that occurs in response to a certain stimulation. For example, the followings determine the type of an event-related potential signal: (1) polarity (positive or negative) of potential; (2) latency (an amount of time from a stimulation until the potential is induced); (3) the amplitude level of potential; and so on.

<Event-Related Potential Characteristic Amount Extraction Section 55>

From the event-related potential received from the biological signal measurement section 50, the characteristic amount extraction section 55 extracts a characteristic amount for each of the first to third sounds.

The characteristic amount of an event-related potential is, for example, time-frequency information of the event-related potential. An example of time-frequency information is information concerning wavelet coefficients. In the following description, each allusion to a "wavelet coefficient" is synonymous to time-frequency information of event-related potential.

In the present embodiment, in accordance with the particulars of the sound stimulations received from the sound stimulation sound pressure determination section 71, the characteristic amount extraction section 55 calculates respective wavelet-coefficient related characteristic amounts for the first to third sounds.

The characteristic amount extraction section 55 sends the calculated characteristic amount and the information of sound stimulations (right or left ear, frequency, sound pressure, etc.) to the hearing aid gain determination section 65. The wavelet-coefficient related characteristic amount may be determined as an average value in a predetermined range which is defined through division by a predetermined breadth on each of the frequency axis and the time axis, for example. For instance, 9 divisions may be made between 2.5 Hz to 12.5 Hz on the frequency axis, and the time axis may be divided into time ranges of every 50 ms; and an average of the wavelet coefficients in such divided ranges may be determined to be the characteristic amount. The breadths on the frequency axis and the time axis by which averaging is to be done for the characteristic amount calculation may be finer or coarser than the above, so long as hearing aid gain estimation is possible.

As described above, it is considered particularly effective for hearing aid output estimation to analyze the periods during which an N1 component and a P2 component would appear in the event-related potential. Therefore, the characteristic amount extraction section 55 may be arranged to calculate time-frequency information (an average of wavelet coefficients) in a zone until the lapse of 300 ms since the point of presenting each of the first sound, the second sound, and the third sound.

<Hearing Aid Gain Determination Section 65>

Based on the respective wavelet-coefficient related characteristic amounts for the first to third sounds received from the characteristic amount extraction section 55, the gain determination section 65 determines a hearing aid gain for each frequency.

The hearing aid gain determination section 65 employs a predetermined criterion (training data, a discriminant function, etc.) to apply a linear discrimination to the received wavelet characteristic amount, thereby making a hearing aid gain estimation. Specifically, the predetermined criterion means, for example, information which previously defines associations between wavelet characteristic amounts and hearing aid gain values. The predetermined criterion may be a table defining associations between wavelet characteristic amounts and hearing aid gain values, or a predetermined equation. The hearing aid gain determination section 65 may retain the predetermined criterion in advance.

The gain determination section 65 may retain a predetermined criterion for each frequency of the sound stimulation group. Alternatively, the gain determination section 65 may be arranged to employ an externally acquired predetermined criterion.

The predetermined criterion may be training data which is generated from the hearing aid gain under a 90 dBSPL input or a 80 dBSPL input, for example. The training data may be generated based on hearing aid gains and wavelet characteristic amounts which are measured by previously conducting the aforementioned hearing aid characteristics measuring experiment and electroencephalogram measurement experiment with respect to at least two other people.

Herein, the sound stimulation conditions concerning the sound pressures and number of sound stimulations in the electroencephalogram measurement experiment for generating the predetermined criterion need to identically conform to the pattern of changing stimulation sound pressure as determined by the sound stimulation sound pressure determination section 71. The predetermined criterion may be retained so as to be itemized for each frequency, based on pooled data of both right and left ears. In that case, based on the information of sound stimulation frequency received from the characteristic amount extraction section 55, the predetermined criterion used in the hearing aid gain measurement may be switched so that the frequency of the one who is the subject of determination matches the frequency of the predetermined criterion.

Moreover, the predetermined criterion may be switched according to the user's symptoms of hypacusia. For example, different predetermined criteria may be applied to general categories such as conductive deafness and perceptive deafness. Also, predetermined criteria may be prepared and switched for different audiogram patterns, e.g., gradual low tone loss or gradual high tone loss. The hearing aid gain determination section 65 sends the determined hearing aid gain to the hearing aid gain setting section 80.

<Hearing Aid Gain Setting Section 80>

The gain setting section 80 allows the hearing aid gain received from the gain determination section 65 to be set in the hearing aid of the user 5, the hearing aid gain having been estimated for each frequency under: (1) a 90 dBSPL input or a 80 dBSPL input; or (2) a 90 dBSPL input and a 80 dBSPL input.

<Processing by Hearing Aid Gain Determination System 100>

Figure 11:
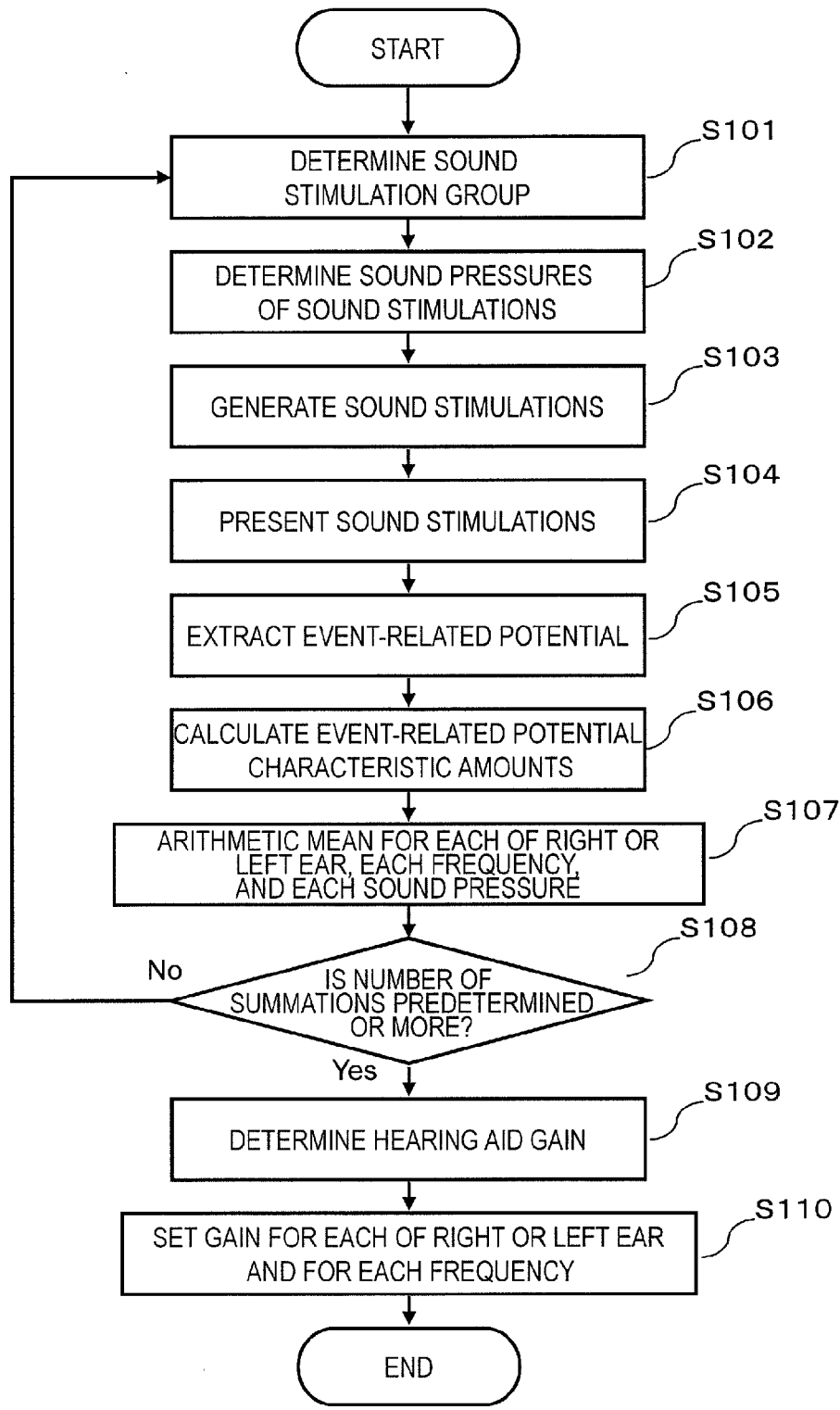
FIG. 11 is a flowchart showing exemplary overall processing by the hearing aid gain determination system in outline.

With reference to FIG. 11, a processing procedure by the gain determination system 100 shown in FIG. 8 will be described. FIG. 11 is a flowchart showing exemplary processing by the gain determination system 100.

(Step S101)

The sound stimulation group determination section 70 determines the ear and frequency for which the sound stimulation group is to be presented, the durations of sound stimulations within the sound stimulation group, and the interval between stimulations. The ear and frequency for presentation may be randomly determined based on the following constraints, for example. No sound stimulation of the same frequency as the immediately previous sound stimulation group is selected. The ear is selected in random order between right and left. However, not more than four sound stimulation groups are successively presented to either the right or left ear. The duration of each sound stimulation is set to e.g. 25 ms or more, so that an auditory evoked potential will be stably induced. Moreover, the interval between stimulations is set to a time which is equal to or greater than the duration of a sound stimulation and equal to or less than 1 second, e.g., 300 ms or 200 ms. The information having been determined of the ear and frequency for which the sound stimulation group is to be presented, the durations of sound stimulations within the sound stimulation group, and the interval between stimulations, is sent to the sound stimulation sound pressure determination section 71.

(Step S102)

From the sound stimulation group determination section 70, the sound pressure determination section 71 receives the information of the ear and frequency for which the sound stimulation group is to be presented, the durations of sound stimulations within the sound stimulation group, and the interval between stimulations. Then, the sound pressures of the first to third sounds in the sound stimulation group are determined to be monotonously descending within a sound pressure range that is lower than a sound pressure which is generally evaluated to be the UCL. For example, the sound pressure of the first sound may be determined to be 80 dBHL, the sound pressure of the second sound to be 75 dBHL, and the sound pressure of the third sound to be 70 dBHL. Alternatively, the sound pressure of the first sound may be determined to be 80 dBHL, the sound pressure of the second sound to be 65 dBHL, and the sound pressure of the third sound to be 50 dBHL. The determined sound pressures of the sound stimulations in the sound stimulation group are sent to the sound stimulation generation section 75, together with the information received from the sound stimulation group determination section 70.

(Step S103)

The sound stimulation generation section 75 generates sound stimulation data based on the sound stimulation information received from the sound pressure determination section 71. Each sound stimulation may be a tone burst sound having a rise and fall of 3 ms and a duration of 44 ms, for example.

(Step S104)

At step S104, the sound stimulation generation section outputs a sound stimulation to the user via the sound stimulation output section 10, and outputs a trigger signal to the biological signal measurement section 50 at that timing. The sound stimulation data may be generated in such a manner that a single piece of sound stimulation data is created for one sound stimulation group, from which a plurality of sound stimulations that undergo changes in sound pressure at a predetermined time interval are derived, for example. In that case, the trigger signal to be sent to the biological signal measurement section 50 may only be sent at the timing of presenting the first sound.

(Step S105)

The biological signal measurement section 50 measures an electroencephalogram as a biological signal. Then, it applies frequency filtering with an appropriate cutoff frequency to the electroencephalogram data, and based on a trigger received from the sound stimulation generation section 75 as a starting point, cuts out an event-related potential in a predetermined zone (e.g., a zone from 100 ms before the first sound presentation to 400 ms after the $n^{th}$ sound presentation), and sends that waveform data (event-related potential) to the characteristic amount extraction section 55.

(Step S106)

In accordance with the particulars of the sound stimulations received from the sound pressure determination section 71, the characteristic amount extraction section 55 calculates respective wavelet-coefficient related characteristic amounts for the first to third sounds from the event-related potentials received from the biological signal measurement section 50. For example, by using a Mexican hat mother wavelet, wavelet coefficients from 2.5 Hz to 12.5 Hz are obtained.

(Step S107)

At step S107, based on the sound stimulation information received from the sound pressure determination section 71, the characteristic amount extraction section 55 takes an arithmetic mean of the wavelet coefficients calculated at step S106 for each of the right or left ear and for each frequency.

(Step S108)

The characteristic amount extraction section 55 determines whether the number of summations in the arithmetic mean for the sound stimulations of the sound stimulation group presented at step S104 has reached a predetermined number of times. If the number of summations is less than the predetermined number of times, the process returns to step S101 to repeat presentation of the sound stimulation group. If the number of summations is equal to or greater than the predetermined number of times, the characteristic amount extraction section 55 sends the arithmetic-meaned wavelet-coefficient related characteristic amount to the hearing aid gain determination section 65, and the process proceeds to step S108. The predetermined number of times may be 20 times, for example. Note that "20 times" is a mere example, although it is a number of summations which is frequently adopted in the fields where event-related potentials are to be measured.

(Step S109)

By using the respective wavelet-coefficient related characteristic amounts of the first to third sounds received from the characteristic amount extraction section 55, the hearing aid gain determination section 65 determines a hearing aid gain. The hearing aid gain determination can be achieved through a linear discrimination utilizing training data (predetermined criterion) that is prepared in advance, which is generated from wavelet characteristic amounts and hearing aid gains under a 90 dBSPL input or a 80 dBSPL input of other people, for example. A number of training data may be prepared for use in hearing aid gain measurement at different frequencies, and switched so that the frequency of the one who is the subject of determination matches the frequency of the training data. The training data may also be switched for each of the right or left ear, in addition to frequency. Moreover, the training data may be switched according to the user's symptoms of hypacusia. For example, training data may be prepared and switched between general categories, e.g., conductive deafness and perceptive deafness. Also, training data may be prepared and switched according to the audiogram pattern, e.g., gradual low tone loss or gradual high tone loss.

(Step S110)

The hearing aid gain setting section 80 allows the hearing aid gain result for each frequency, which is received from the gain determination section 65, to be set to the hearing aid of the user 5.

With the hearing aid gain determination system 100 of the present embodiment, for example, three pure tones of the same frequency with monotonously descending sound pressures are presented, and electroencephalographic characteristic amounts in response to the respective sound stimulations from first to third sounds are extracted. From the pattern of changing characteristic amounts, a hearing aid gain for each frequency can be directly measured under: (1) a 90 dBSPL input or a 80 dBSPL input; or (2) a 90 dBSPL input and a 80 dBSPL input. As a result, the precision concerning the compression ratio of a hearing aid of non-linear amplification type is improved, and a hearing aid fitting can be realized which provides more than satisfactory hearing while a hearing aid is worn.

In the description of the present embodiment, the biological signal measurement section 50 cuts out an event-related potential in a predetermined range based on a trigger signal from the sound stimulation generation section 75 as a starting point, and sends it to the characteristic amount extraction section 55. However, this process is an example. In another process, for example, the biological signal measurement section 50 may constantly measure an electroencephalogram, and the characteristic amount extraction section 55 may perform cutting out of an event-related potential and a baseline correction as needed. With such construction, the sound stimulation generation section 75 does not need to send a trigger signal to the biological signal measurement section 50, but may send a trigger signal to the event-related potential characteristic amount extraction section 55.

Although the present embodiment illustrates that the result of hearing aid gain measurement is set to the hearing aid of the user 5 by the hearing aid gain setting section 80, this is not essential. For example, in the case where the hearing aid gain setting section 80 is provided external to the hearing aid gain determination apparatus 1, each result of determination by the hearing aid gain determination section 65 may simply be output, or accumulated. Thus, each result of determination becomes available as information for hearing aid gain setting.

Figure 12:
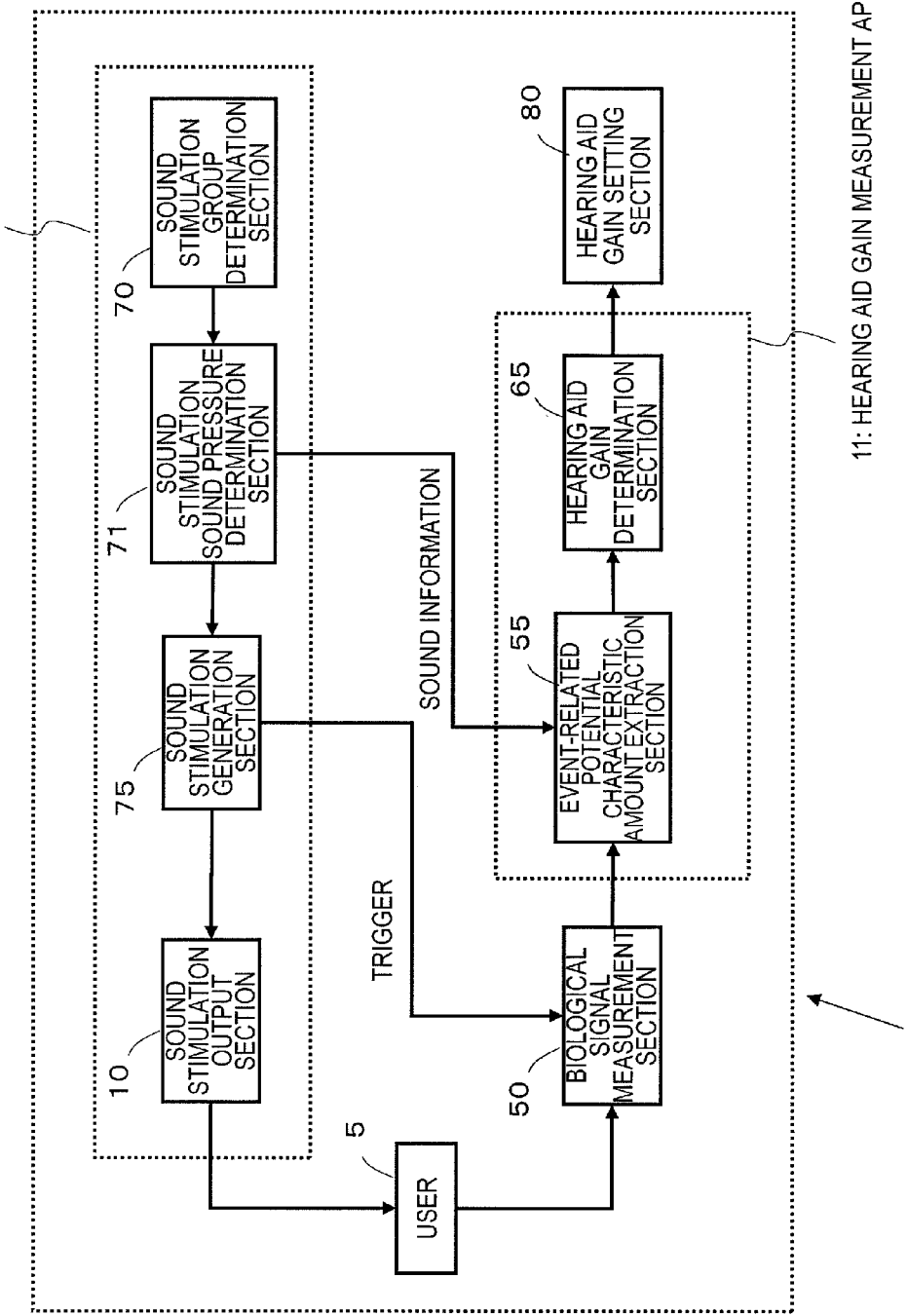
FIG. 12 is a diagram showing a variant of the construction according to Embodiment 1.

Moreover, as shown in FIG. 12, the hearing aid gain determination system 100 may include a hearing aid gain determination apparatus 11, a sound stimulation apparatus 12, the biological signal measurement section 50, and the hearing aid gain setting section 80. The hearing aid gain determination apparatus 11, the sound stimulation apparatus 12, biological signal measurement section 51, and the hearing aid gain setting section 80 are interconnected in a wired or wireless manner for exchange of information.

The hearing aid gain determination apparatus 11 includes the event-related potential characteristic amount extraction section 55 and the hearing aid gain determination section 65. The sound stimulation apparatus 12 includes the sound stimulation output section 10, the sound stimulation group determination section 70, the sound stimulation sound pressure determination section 71, and the sound stimulation generation section 75.

The event-related potential characteristic amount extraction section 55 of the hearing aid gain determination apparatus 11 receives an electroencephalogram measured by the biological signal measurement section 50, and sound stimulation group information which is output from the sound stimulation output section 10.

Similarly to the above, from an electroencephalogram signal which is measured by the biological signal measurement section 50, the event-related potential characteristic amount extraction section 55 extracts a characteristic amount concerning the time-frequency information of an event-related potential which is contained in a predetermined time range after a point in time of presenting each sound stimulation in the sound stimulation group. Based on the characteristic amount extracted by the characteristic amount extraction section, the hearing aid gain determination section 65 determines a hearing aid gain for the frequency of the sound stimulation group, against a predetermined criterion.

The hearing aid gain determination system according to the present disclosure is able to determine a hearing aid gain from the electroencephalogram of a given user, and thus is useful for the adjustment of a hearing aid at a hearing aid shop or in households, etc.

While the present disclosure has been described with respect to preferred embodiments thereof, it will be apparent to those skilled in the art that the present disclosure may be modified in numerous ways and may assume many embodiments other than those specifically described above. Accordingly, it is intended by the appended claims to cover all modifications of the disclosure that fall within the true spirit and scope of the invention.

What is claimed is:

1. A hearing aid gain determination system comprising:
one or more memories; and
circuitry which in operation is configured to:
measure an electroencephalogram signal of a user;
determine a frequency of a sound stimulation group including a first sound, a second sound, and a third sound, the first to third sounds being pure tones and having a same frequency;
determine sound pressures of the first sound, the second sound, and the third sound so that the respective sound pressures are equal to or less than a predetermined threshold value and that the first sound, the second sound, and the third sound consecutively decrease in sound pressure in this order;
present the first sound, the second sound, and the third sound to the user at the determined frequency and sound pressures;
extract a characteristic amount concerning time-frequency information of an event-related potential in the electroencephalogram signal in a predetermined time range beginning after a point of presenting each of the first sound, the second sound, and the third sound, the characteristic amount of the event-related potential being extracted based on at least one of an N1 component in response to the first sound, a P2 component in response to the second sound, and a P2 component in response to the third sound; and
determine a hearing aid gain for the frequency of the sound stimulation group against a predetermined criterion based on the characteristic amounts extracted by the circuitry.

2. The hearing aid gain determination system of claim 1, wherein the circuitry is configured to determine a hearing aid output under an input sound pressure of 80dBSPL or more against a predetermined criterion which previously defines associations between the characteristic amounts and hearing aid output values which are set under an input sound pressure of 80dBSPL or more.

3. The hearing aid gain determination system of claim 2, wherein the circuitry is configured to determine a hearing aid output under an input sound pressure having a 90dBSPL or 80dBSPL against a predetermined criterion which previously defines associations between the characteristic amounts and hearing aid output values under a 90dBSPL input or a 80dBSPL input.

4. The hearing aid gain determination system of claim 1, wherein the predetermined threshold value is a sound pressure lower than a generic uncomfortable level (UCL) value.

5. The hearing aid gain determination system of claim 1, wherein the circuitry is configured to determine the sound pressures of the first sound, the second sound, and the third sound so that the first sound, the second sound, and the third sound consecutively decrease in sound pressure in this order by every 5 dB.

6. The hearing aid gain determination system of claim 1, wherein the circuitry is configured to determine the sound pressures of the first sound, the second sound, and the third sound so that the first sound, the second sound, and the third sound consecutively decrease in sound pressure in this order by every 15 dB.

7. The hearing aid gain determination system of claim 3, wherein the circuitry further is configured to set a hearing aid gain for each frequency under: a 90dBSPL input or a 80dBSPL input; or a 90dBSPL input and a 80dBSPL input, based on a result of the determination of the hearing aid output.

8. The hearing aid gain determination system of claim 3, wherein the circuitry is configured to retain, as the predetermined criterion, data which defines associations between time-frequency related characteristic amounts measured of a plurality of users and hearing aid gains under a 90dBSPL input or a 80dBSPL input, and determines a hearing aid gain against the predetermined criterion.

9. The hearing aid gain determination system of claim 1, wherein the circuitry is configured to retain said predetermined criterions respectively for different frequencies of the sound stimulation group, and uses a selected one of the predetermined criterions in accordance with the frequency of the sound stimulation group.

10. The hearing aid gain determination system of claim 1, wherein the circuitry is configured to calculate time-frequency information of the electroencephalogram signal in a zone until the lapse of 300 ms since the point of presenting each of the first sound, the second sound, and the third sound, and adopts as a characteristic amount an averaged value over a predetermined frequency range and a predetermined time range.

11. The hearing aid gain determination system of claim 10, wherein the predetermined frequency range is a frequency range defined by dividing a frequency range from 2.5 Hz to 12.5 Hz into nine.

12. The hearing aid gain determination system of claim 10, wherein the predetermined time range is 50 ms.

13. A hearing aid gain determination apparatus comprising:
one or more memories; and
circuitry which in operation is configured to:
extract, from an electroencephalogram signal of a user measured by an electroencephalograph, a time-frequency related characteristic amount of an event-related potential in the electroencephalogram signal after a point of presenting each of a first sound, a second sound, and a third sound from an output section, the first sound, the second sound, and the third sound having a same frequency and consecutively decreasing in sound pressure in this order such that the respective sound pressures are equal to or less than a predetermined threshold value, the characteristic amount of the event-related potential being extracted based on at least one of an N1 component in response to the first sound, a P2 component in response to the second sound, and a P2 component in response to the third sound; and
determine a hearing aid gain against a predetermined criterion based on the characteristic amounts extracted by the circuitry.

14. A hearing aid gain determination method comprising the steps of:
measuring an electroencephalogram signal of a user;
determining a frequency of a sound stimulation group including a first sound, a second sound, and a third sound, the first to third sounds being pure tones and having a same frequency;
determining sound pressures of the first sound, the second sound, and the third sound so that the respective sound pressures are equal to or less than a predetermined threshold value and that the first sound, the second sound, and the third sound consecutively decrease in sound pressure in this order;
presenting the first sound, the second sound, and the third sound to the user at the determined frequency and sound pressures;
extracting a characteristic amount concerning time-frequency information of an event-related potential in the electroencephalogram signal in a predetermined time range beginning after a point of presenting each of the first sound, the second sound, and the third sound, the characteristic amount of the event-related potential being extracted based on at least one of an N1 component in response to the first sound, a P2 component in response to the second sound, and a P2 component in response to the third sound; and
based on the extracted characteristic amounts, determining a hearing aid gain against a predetermined criterion.

15. A non-transitory computer-readable medium storing a computer program to be executed by a computer mounted in a hearing aid gain determination apparatus of a hearing aid gain determination system,
wherein the computer program causes the computer to execute the steps of:
determining a frequency of a sound stimulation group including a first sound, a second sound, and a third sound, the first to third sounds being pure tones and having a same frequency;
determining sound pressures of the first sound, the second sound, and the third sound so that the respective sound pressures are equal to or less than a predetermined threshold value and that the first sound, the second sound, and the third sound consecutively decrease in sound pressure in this order;
presenting the first sound, the second sound, and the third sound to a user at the determined frequency and sound pressures;
from an electroencephalogram signal of the user when the first sound, the second sound, and the third sound are presented thereto, extracting a characteristic amount concerning time-frequency information of an event-related potential in a predetermined time range beginning after a point of presenting each of the first sound, the second sound, and the third sound, the characteristic amount of the event-related potential being extracted based on at least one of an N1 component in response to the first sound, a P2 component in response to the second sound, and a P2 component in response to the third sound; and
based on the extracted characteristic amounts, determining a hearing aid gain against a predetermined criterion.

16. The hearing aid gain determination system of claim 1, wherein the circuitry further is configured to set a hearing aid gain based on the hearing aid gain determination.

17. The hearing aid gain determination apparatus of claim 13, wherein the circuitry further is configured to set a hearing aid gain based on the hearing aid gain determination.

18. The hearing aid gain determination method of claim 14, further comprising a step of setting a hearing aid gain based on the hearing aid gain determination.

19. The non-transitory computer-readable medium of claim 15, wherein the computer program further causes the computer to execute a step of setting a hearing aid gain based on the hearing aid gain determination.

20. The hearing aid gain determination system of claim 1, wherein the circuitry determines a hearing aid gain for a 90dBSPL input based on a P2 component in response to the third sound, and a hearing aid gain for an 80dBSPL input based on an N1 component in response to the first sound.

* * * * *